US012265004B2

(12) United States Patent
Boyden et al.

(10) Patent No.: US 12,265,004 B2
(45) Date of Patent: Apr. 1, 2025

(54) MEMBRANE PROBES FOR EXPANSION MICROSCOPY

(71) Applicant: Massachusetts Institute of Technology, Cambridge, MA (US)

(72) Inventors: Edward Stuart Boyden, Chestnut Hill, MA (US); Jeong Seuk Kang, Cambridge, MA (US); Emmanouil D. Karagiannis, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 906 days.

(21) Appl. No.: 17/089,003

(22) Filed: Nov. 4, 2020

(65) Prior Publication Data
US 2021/0130882 A1    May 6, 2021

Related U.S. Application Data

(60) Provisional application No. 62/930,938, filed on Nov. 5, 2019.

(51) Int. Cl.
| | |
|---|---|
| *G01N 1/36* | (2006.01) |
| *C07K 7/06* | (2006.01) |
| *G01N 1/30* | (2006.01) |
| *G02B 21/36* | (2006.01) |

(52) U.S. Cl.
CPC ............... *G01N 1/36* (2013.01); *C07K 7/06* (2013.01); *G01N 1/30* (2013.01); *G01N 2001/364* (2013.01); *G02B 21/36* (2013.01)

(58) Field of Classification Search
None
See application file for complete search history.

(56) References Cited

U.S. PATENT DOCUMENTS

| | | |
|---|---|---|
| 5,840,862 A | 11/1998 | Bensimon et al. |
| 5,952,232 A | 9/1999 | Rothman |
| 6,107,081 A | 8/2000 | Feeback et al. |

(Continued)

FOREIGN PATENT DOCUMENTS

| | | |
|---|---|---|
| CN | 104350372 A | 2/2015 |
| CN | 111848855 A | 10/2020 |

(Continued)

OTHER PUBLICATIONS

Ahearn et al., Posttranslational Modifications of RAS Proteins, Cold Spring Harb Perspect Med 2018;8:a031484 (Year: 2018).*

(Continued)

*Primary Examiner* — Paul S Hyun
*Assistant Examiner* — Mickey Huang
(74) *Attorney, Agent, or Firm* — Pierce Atwood LLP

(57) ABSTRACT

The present invention provides compositions and methods that allow lipid membranes to be imaged optically at nanoscale resolution via a lipid-optimized form of expansion microscopy, also referred to as membrane expansion microscopy (mExM). mExM, via a post-expansion antibody labeling protocol, enables protein-lipid relationships to be imaged in organelles such as mitochondria, the endoplasmic reticulum, the nuclear membrane, and the Golgi apparatus. mExM may be of use in a variety of biological contexts, including the study of cell-cell interactions, intracellular transport, and neural connectomics.

22 Claims, 10 Drawing Sheets

Specification includes a Sequence Listing.

(56) References Cited

U.S. PATENT DOCUMENTS

| | | |
|---|---|---|
| 6,204,064 B1 | 3/2001 | Alberts et al. |
| 6,271,278 B1 | 8/2001 | Park et al. |
| 6,287,870 B1 | 9/2001 | Wardlaw |
| 6,548,255 B2 | 4/2003 | Bensimon et al. |
| 9,376,677 B2 | 6/2016 | Mir |
| 10,059,990 B2 | 8/2018 | Boyden et al. |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,526,649 B2 | 1/2020 | Chen et al. |
| 10,563,257 B2 | 2/2020 | Boyden et al. |
| 10,774,367 B2 | 9/2020 | Fraser et al. |
| 10,995,361 B2 | 5/2021 | Chen et al. |
| 11,180,804 B2 | 11/2021 | Chen et al. |
| 11,408,890 B2 | 8/2022 | Boyden et al. |
| 2002/0176880 A1 | 11/2002 | Cruise et al. |
| 2003/0120231 A1 | 6/2003 | Wang et al. |
| 2004/0115629 A1 | 6/2004 | Panzer et al. |
| 2004/0137527 A1 | 7/2004 | Sleytr et al. |
| 2004/0209317 A1* | 10/2004 | Ting ............ C12N 9/93 435/7.5 |
| 2004/0248326 A1 | 12/2004 | Ziaie et al. |
| 2005/0034990 A1 | 2/2005 | Crooks et al. |
| 2005/0069877 A1 | 3/2005 | Gandhi et al. |
| 2005/0090016 A1 | 4/2005 | Rich et al. |
| 2005/0169962 A1 | 8/2005 | Bhatia et al. |
| 2005/0196702 A1 | 9/2005 | Bryant et al. |
| 2006/0000767 A1 | 1/2006 | Trauger et al. |
| 2006/0003356 A1 | 1/2006 | Shaw et al. |
| 2006/0110760 A1 | 5/2006 | Kim et al. |
| 2006/0115146 A1 | 6/2006 | Ogura et al. |
| 2006/0165912 A1 | 7/2006 | Koberstein et al. |
| 2007/0023942 A1 | 2/2007 | Andino et al. |
| 2007/0026432 A1 | 2/2007 | Ke et al. |
| 2007/0042954 A1 | 2/2007 | Chen et al. |
| 2007/0134902 A1 | 6/2007 | Bertino et al. |
| 2007/0177786 A1 | 8/2007 | Bartels |
| 2008/0139407 A1 | 6/2008 | Slootstra et al. |
| 2008/0261834 A1 | 10/2008 | Simon |
| 2008/0286360 A1 | 11/2008 | Shoichet |
| 2009/0011141 A1 | 1/2009 | Carter et al. |
| 2009/0011420 A1 | 1/2009 | Barron et al. |
| 2009/0096133 A1 | 4/2009 | Doyle et al. |
| 2009/0191627 A1 | 7/2009 | Fadeev et al. |
| 2009/0241681 A1 | 10/2009 | Machauf et al. |
| 2010/0041128 A1 | 2/2010 | Banes et al. |
| 2010/0055161 A1 | 3/2010 | Ahn |
| 2010/0056445 A1 | 3/2010 | Sharma et al. |
| 2010/0068725 A1 | 3/2010 | Armbruster et al. |
| 2010/0096334 A1 | 4/2010 | Edmiston |
| 2010/0111396 A1 | 5/2010 | Boucheron |
| 2010/0119755 A1 | 5/2010 | Chung et al. |
| 2010/0248977 A1 | 9/2010 | Johnston et al. |
| 2010/0291357 A1 | 11/2010 | Polizzotti et al. |
| 2011/0009171 A1 | 1/2011 | Watanabe et al. |
| 2011/0070604 A1 | 3/2011 | Gimzewski et al. |
| 2011/0087315 A1 | 4/2011 | Richardson-Burns et al. |
| 2011/0091717 A1 | 4/2011 | Weiss |
| 2011/0091922 A1 | 4/2011 | Krishnan et al. |
| 2011/0291357 A1 | 12/2011 | Boyle |
| 2012/0025271 A1 | 2/2012 | Nakano |
| 2012/0184670 A1 | 7/2012 | Kobayashi et al. |
| 2012/0220478 A1 | 8/2012 | Shaffer |
| 2012/0251527 A1 | 10/2012 | Reiser |
| 2012/0310223 A1 | 12/2012 | Knox et al. |
| 2013/0045503 A1 | 2/2013 | Miyawaki et al. |
| 2013/0203605 A1 | 8/2013 | Shendure et al. |
| 2014/0087139 A1 | 3/2014 | Rowley et al. |
| 2014/0193651 A1 | 7/2014 | Kharlampieva et al. |
| 2014/0364330 A1 | 12/2014 | Mershin et al. |
| 2015/0086103 A1 | 3/2015 | Tsunomori |
| 2015/0087001 A1 | 3/2015 | Gradinaru et al. |
| 2015/0226743 A1 | 8/2015 | Weiss et al. |
| 2015/0353989 A1 | 12/2015 | Fraser et al. |
| 2015/0370961 A1 | 12/2015 | Zhang et al. |
| 2015/0376261 A1 | 12/2015 | Steyaert et al. |
| 2016/0116384 A1 | 4/2016 | Chen et al. |
| 2016/0252528 A1 | 9/2016 | Sangaralingham et al. |
| 2016/0265046 A1 | 9/2016 | Zhang et al. |
| 2016/0304952 A1 | 10/2016 | Boyden et al. |
| 2016/0305856 A1 | 10/2016 | Boyden et al. |
| 2017/0067096 A1 | 3/2017 | Wassie et al. |
| 2017/0081489 A1 | 3/2017 | Rodriques et al. |
| 2017/0087489 A1 | 3/2017 | Terlingen et al. |
| 2017/0089811 A1 | 3/2017 | Tillberg et al. |
| 2017/0103521 A1 | 4/2017 | Chukka et al. |
| 2017/0182220 A1 | 6/2017 | Song et al. |
| 2017/0199104 A1 | 7/2017 | Gradinaru et al. |
| 2017/0276598 A1 | 9/2017 | Ikuyama |
| 2017/0323431 A1 | 11/2017 | Sarkar et al. |
| 2018/0119219 A1 | 5/2018 | Chen et al. |
| 2019/0064037 A1 | 2/2019 | Boyden et al. |
| 2019/0071656 A1 | 3/2019 | Chang et al. |
| 2019/0113423 A1 | 4/2019 | Goodman et al. |
| 2019/0194709 A1 | 6/2019 | Church et al. |
| 2019/0256633 A1 | 8/2019 | Gao et al. |
| 2020/0041514 A1 | 2/2020 | Boyden et al. |
| 2020/0049599 A1 | 2/2020 | Alexander et al. |
| 2020/0081005 A1 | 3/2020 | Boyden et al. |
| 2020/0217853 A1 | 7/2020 | Estandian et al. |
| 2020/0271556 A1 | 8/2020 | Sarkar et al. |
| 2020/0277664 A1 | 9/2020 | Frenz |
| 2021/0190652 A1 | 6/2021 | Quevedo et al. |
| 2021/0196856 A1 | 7/2021 | Boyden et al. |

FOREIGN PATENT DOCUMENTS

| | | |
|---|---|---|
| CN | 112574089 A | 3/2021 |
| EP | 3159361 A1 | 4/2017 |
| JP | 2005291759 A | 10/2005 |
| JP | 2006036957 A | 2/2006 |
| JP | 2008286694 A | 11/2008 |
| JP | 2009191125 A | 8/2009 |
| JP | 2014005231 | 1/2014 |
| WO | 2000008212 A1 | 2/2000 |
| WO | 2007103665 A2 | 9/2007 |
| WO | 2008058302 A1 | 5/2008 |
| WO | 2010048605 A1 | 4/2010 |
| WO | 2012112689 A1 | 8/2012 |
| WO | 2012142664 A1 | 10/2012 |
| WO | 2014025392 A1 | 2/2014 |
| WO | 2014152984 A1 | 9/2014 |
| WO | 2015041755 A1 | 3/2015 |
| WO | 2015127183 A2 | 8/2015 |
| WO | 2016040489 A1 | 3/2016 |
| WO | 2017027367 A1 | 2/2017 |
| WO | 2017027368 A1 | 2/2017 |
| WO | 2017031249 | 2/2017 |
| WO | 2017079406 A1 | 5/2017 |
| WO | 2017147435 A1 | 8/2017 |
| WO | 2018157074 A1 | 8/2018 |
| WO | 2019144391 A1 | 8/2019 |
| WO | 2021051011 A1 | 3/2021 |
| WO | 2021183667 A1 | 9/2021 |
| WO | 2022100696 A1 | 3/2022 |

OTHER PUBLICATIONS

Hamano et al., ε-Poly-L-Lysine Peptide Chain Length Regulated by the Linkers Connecting the Transmembrane Domains of ε-Poly-L-Lysine Synthetase, Aug. 2014, Applied and Environmental Microbiology, vol. 80 No. 16, p. 4993-5000 (Year: 2014).*

Kleuss et al., Galphas is palmitoylated at the N-terminal glycine, The EMBO Journal vol. 22 No. 4 pp. 826-832, 2003 (Year: 2003).*

Salaun et al., The intracellular dynamic of protein palmitoylation, 2010, J. Cell Biol. vol. 191 No. 7 1229-1238 (Year: 2010).*

Guan et al., Understanding Protein Palmitoylation: Biological Significance and Enzymology, 2011, Sci China Chem. Dec. 2011; 54(12): 1888-1897 (Year: 2011).*

Abbasi et al., Palmitic Acid-Modified Poly-L-Lysine for Non-Viral Delivery of Plasmid DNA to Skin Fibroblasts, 2007, Biomacromolecules 2007, 8, 1059-1063 (Year: 2007).*

(56) References Cited

OTHER PUBLICATIONS

Wen et al., Specific antibody immobilization with biotin-poly(L-lysine)-g-poly(ethylene glycol) and protein A on microfluidic chips, Journal of Immunological Methods 350 (2009) 97-105 (Year: 2009).*
Filonov, G. S. et al. "Bright and stable near-infrared fluorescent protein for in vivo imaging." Nat. Biotechnol. 29, 757-61 (2011).
Fouz, M. et al., "Bright Fluorescent Nanotags from Bottlebrush Polymers with DNATipped Bristles," ACS Central Science, vol. 1, 2015, 431-438.
Freifeld, L. et al., "Expansion microscopy of zebrafish for neuroscience and developmental biology studies," PNAS (online), Nov. 21, 2017, E10799-E10808.
Goedhardt, J. et al. "Structure-guided evolution of cyan fluorescent proteins towards a quantum yield of 93%." Nat. Commun. 3, 751 (2012).
Goor, Olga J. et al., "Introduction of anti-fouling coutings at the surface of supramolecular elastomeric materials via post-modification of reactive supramolecular additives," Polymer Chem., vol. 8, No. 34, Jan. 1, 2017, 5228-5238.
Griesbeck, et al., "Reducing the environmental sensitivity of yellow fluorescent protein. Mechanism and applications," J. Biol. Chem., 276, 2001, 29188-94.
Guo A. et al. "The Critical Role of Surface Chemistry In Protein Microarrays" in Functional Protein Microarrays in Drug Discovery, edt. Paul Predki, p. 53-71 (CRC press, Boca Raton, 2007).
Guo, H. et al. "An efficient procedure for protein extraction from formalin-fixed, Paraffin-embedded tissues for reverse phase protein arrays." Proteome Sci. 10:56 (2012). doi: 10.1186/1477-5956-10-56.
Gurskaya, N. G. et al. "Engineering of a monomeric green-to-red photoactivatable fluorescent protein induced by blue light." Nat. Biotechnol. 24, 461-5 (2006).
Gyorvary, E. S. et al., "Self-Assembly and Recrystallization of Bacterial S-Layer Proteins at Silicon Supports Imaged in Real Time by Atomic Force Microscopy," Journal of Microscopy, vol. 212, 2003, 300-306.
Habuchi, S. et al., "mKikGR, a monomeric photoswitchable fluorescent protein," PLoS One, 3, 2008, e3944.
Hackstadt, T. , "Steric hindrance of antibody binding to surface proteins of Coxiella burnetti by phase I lipopolysaccharide," Infect Immun, 56, 1998, 802-807.
Heim, R. et al., "Engineering green fluorescent protein for improved brightness, longer wavelengths and fluorescence resonance energy transfer," Curr. Biol., 6, 1996, 178-82.
Heim, R. et al., "Wavelength mutations and posttranslational autoxidation of green fluorescent protein," Proc. Natl. Acad. Sci. U.S.A., 91, 1994, 12501-4.
Hoffman, T. L. et al., "A Biosensor Assay for Studying Ligand-Membrane Receptor Interactions: Binding of Antibodies and HIV-1 Env to Chemokine Receptors," PNAS, 97(21), 2000, 11215-11220.
Honig, M. G. et al. "DiI and DIO: versatile fluorescent dyes for neuronal labeling and pathway tracing." Trends Neurosci. 12(9):333-341 (1989). doi:10.1016/0166-2236(89)90040-4.
Honig, M. G. et al. "Fluorescent carbocyanine dyes allow living neurons of identified origin to be studied in long-term cultures." J. Cell Biol. 103:171-187 (1986). doi: 10.1083/jcb.103.1.171.
Huang, B. et al., "Whole-cell 3D Storm reveals interactions between cellular structures with nanometer-scale resolution," Nat. Methods, 5, 2008, 104 7-1052.
Huisken, J. et al., "Optical Sectioning Deep Inside Live Embryos by Selective Plane Illumination Microscopy" Science Aug. 13, 2004 vol. 305 Iss. 5686, p. 1007-9.
Hunt et al. "High temperature antigen retrieval and loss of nuclear morphology: a comparison of microwave and autoclave techniques," J Clin Pathol 1996;49:767-770.
Jamur, M. C. et al. "Permeabilization of Cell Membranes." in Immunocytochemical Methods and Protocols 588:63-6 (2010). doi:10.1007/978-1-59745-324-0_9.
Jekel, P A. et al., "Use of endoproteinase Lys-C from Lysobacter enzymogenes in protein sequence analysis," Anal. Biochem., 134, 1983, 347-354.
Jiang, Y. et al., "Click hydrogels, microgels and nanogels: emerging platforms for drug delivery and tissue engineering," Biomaterials, vol. 35, No. 18, Jun. 1, 2014, 4969-4985.
Jimenez, N. et al., "A Novel Approach for Intracellular 3D Immuno-Labeling for Electron Tomography," Traffic, 13, 2012, 926-933.
Jung, H. et al., "Axonal mRNA localization and local protein synthesis in nervous system assembly, maintenance and repair," Nat. Rev. Neurosci., vol. 13(5), 2012, 308-24.
Kakimoto, K. et al., "Hypothesis for the mechanism for heat-induced antigen retrieval occurring on fresh frozen sections without formalin-fixation in immunohistochemistry," J Mol Histol., 39, 2008, 389-399.
Kaur, et al., "Thermodynamic, Counterion, and Hydration Effects for the Incorporation of Locked Nucleic Acid Nucleotides into DNA Duplexes" Biochemistry 45, 2006, 7347-7355.
Ke R, et al. "In situ sequencing for RNA analysis in preserved tissue and cells." Nat Methods. Sep. 2013; 10(9):857-60. Epub Jul. 14, 2013.
Ke, R. et al., [Supplementary Material] "In situ sequencing for RNA analysis in preserved tissue and cells," Nature Methods 10(9):857-60, 2013, 1-29.
Kroon, D.J , "B-spline Grid, Image and Point based Registration," Matlab Cent. At <http://www.mathworks.com/matlabcentral/fileexchange/20057-b-spline-grid--image-and-point-based-registration>.
Ku, T. et al. "Multiplexed and scalable super-resolution imaging of three-dimensional protein localization in size-adjustable tissues." Nat. Biotechnol. 34(9): 973-981 (2016). doi:10.1038/nbt.3641.
Laemmli, U. K. "Cleavage of structural proteins during the assembly of the head of bacteriophage T4." Nature 227. 680-685 (1970).
Lakkaraju, A. K. K. et al. "Palmitoylated calnexin is a key component of the ribosome-translocon complex." EMBO J. 31, 1823-1835 (2012). doi:10.1038/emboj.2012.15.
Lam, A. J. et al. "Improving FRET dynamic range with bright green and red fluorescent proteins." Nat. Methods 9, 1005-12 (2012).
Lee et al. "Highly multiplexed subcellular RNA sequencing in situ" Sciencexpress. Feb. 27, 2014, pp. 1-6.
Lein, E. et al., "Genome-wide atlas of gene expression in the adult mouse brain," Nature, vol. 445, 2007, 168-76.
Levsky, J. et al., "Fluorescence in situ hybridization: past, present and future," Journal of Cell Science, 116, 2003, 2833-2838.
Lieberman-Aiden, E. et al., "Comprehensive mapping of long-range interactions reveals folding principles of the human genome", Science 326, 2009, 289-93.
Linder, M. E. et al. "Palmitoylation: Policing protein stability and traffic." Nature Reviews Molecular Cell Biology 8:74-84 (2007). doi:10.1038/nrm2084.
Livet, J. et al. "Transgenic strategies for combinatorial expression of fluorescent proteins in the nervous system." Nature 450, 56-62 (2007).
Lowe, D. G., "Distinctive Image Features from Scale-Invariant Keypoints," Int. J. Comput. Vis., 60, 2004, 91-110.
Lubeck, E. et al., "Single-cell in situ RNA profiling by sequential hybridization," Nature Methods, vol. 11 (4), 2014, 360-1.
Lubeck, E. et al., "Single-cell systems biology by super-resolution imaging and combinatorial labeling," Nature Methods, vol. 9, 2012, 743-8.
Mabrey, S. et al. "Investigation of phase transitions of lipids and lipid mixtures by sensitivity differential scanning calorimetry." Proc. Natl. Acad. Scl. 73(11): 3862-3866 (1976). doi:10.1073/pnas.73.11.3862.
Majcher, M. J. et al., "Hydrogel synthesis and design," in 'Cellulose-Based Superabsorbent Hydrogels', Springer International Publishing, Jan. 1, 2018, 1-41.
Markwardt, M. L. et al., "An improved cerulean fluorescent protein with enhanced brightness and reduced reversible photoswitching." PLoS One, 6, 2011, e17896.
McKinney, S. A. et al., "A bright and photostable photoconvertible fluorescent protein," Nat. Methods, 6, 2009, 131-3.

(56) References Cited

OTHER PUBLICATIONS

Meng, H., "Localization of a Blood Pressure Quantitative Trait Locus (QTL) to a 1.7cM Interval on Rat Chromosome 9," Medical College of Ohio, dissertation, 2002, 1-158.
Menon, A. K. "Lipid modifications of proteins." in 'Biochemistry of Lipids, Lipoproteins and Membranes' 39-58 (2008). doi:10.1016/B978-044453219-0.50004-0.
Mito, M. et al., "Simultaneous multicolor detection of RNA and proteins using superresolution microscopy," Methods, doi:10.1016/j.ymeth.2015.11.007., 2015.
Abcam, "IHC-Paraffin Protocol (IHC-P)", 13 pages, published: Jun. 15, 1999, online webpage: www.abcam.com/ps/pdf/protocols/ihc_p.pdf. (Year: 1999).
Mortensen, K. I. et al., "Optimized localization analysis for singlemolecule tracking and super-resolution microscopy", Nat. Methods, 7, 2010, 377-81.
Myhill, N. et al. "The subcellular distribution of calnexin is mediated by PACS-2." Mol. Biol. Cell 19:2777~2788 (2008). doi:10.1091/mbc.E07-10-0995.
Nagai, T. et al. "A variant of yellow fluorescent protein with fast and efficient maturation for cell-biological applications" Nat. Blotechnol. 20, 87-90 (2002).
Nagre, R. D. et al., "Thermosaline Resistant Acrylamide-Based Polyelectrolyte as Filtration Control Additive in Aqueous-Based Mud, Petroleum and Coal," vol. 56, No. 3, 2014, 222-230.
New England Bio Labs, Proteinase K, P8102S product datasheet, 1 page, accessed Nov. 17, 2020.
Nilsson, M. et al., "RNA-templated DNA ligation for transcript ananlysis," Nucleic Acids Research, Information Retrieval LTD., vol. 29, No. 2, Jan. 15, 2001, 578-581.
Orakdogen, N. et al., "Correlation Between Crosslinking Efficiency and Spatial Inhomogeneity in Poly(acrylamide) Hydrogels," Polymer Bulletin, vol. 57, 2006, 631-641.
Ormo, M. et al. "Crystal structure of the Aequorea victoria green fluorescent protein." Science 273, 1392-5 (1996).
Oshima, K. et al., "Model Polyelectrolyte Gels Synthesized by End-Linking of Tetra-Arm Polymers with Click Chemistry: Synthesis and Mechanical Properties," Macromolecules, vol. 47, 2014, 7573-7580.
Panning, B. et al., "X chromosome Inactivation is Mediated by by Xist RNA stabilization," Cell. vol. 90, 1997, 907-16.
Parang et al. "Myeloid translocation genes differentially regulate colorectal cancer programs," Oncogene, Jun. 2016, 35, 6341-6349.
Park, Y. N. et al., "Detection of Hepatitis C Virus RNA Using Ligation-Dependent Polymerase Chain Reaction in Formalin-Fixed, Paraffin-Embedded Liver Tissues," Amer. J. of Pathol., vol. 149, No. 5. Nov. 1, 1996, 1485-1491.
Plath, K. et al., "Xist RNA and the mechanism of X chromosome inactivation," Annu. Rev. Genet. 36, 2002, 233-78.
Product information brochure, Flocryl TM MBA, SNF Floerger, pp. 1-4, accessed 1744136.
Proteinase K from Tritirachium album, solution, Serva Electrophoresis, Instruction Manual, Cat. No. 33755, 1 page, publicly available prior to Feb. 1, 2017.
Pum, D. et al., "Reassembly of S-Layer Proteins", Nanotechnology, 2014, 1-15.
Raj, A. et al., "Detection of individual endogenous RNA transcripts in situ using multiple singly labeled probes," Methods in Enzymology, vol. 472 (Elsevier Inc.), 2010, 365-386.
Raj, A. et al., "Imaging individual mRNA molecules using multiple singly labeled probes," Nat. Methods 5(10), 2008, 877-879.
Randall, K. J. et al., "A dual-label technique for the immunohistochemical demonstration of T-lymphocyte subsets in formalin-fixed, paraffin-embedded rat lymphoid tissue," Toxicol. Pathol., 36, 2008, 795-804.
Rego, E. H. et al. "Nonlinear structured-illumination microscopy with a photoswitchable protein reveals cellular structures at 50-nm resolution." Proc. Natl. Acad. Sci. U. S. A. 109, E135-43 (2012).
Reinhart-King, C. A. et al., "Dynamics and Mechanics of Endothelial Cell Spreading," Biophysical J, 89(1):, Jul. 1, 2005, 676-689.
Revelo, N. H. et al. "A new probe for super-resolution imaging of membranes elucidates trafficking pathways." J. Cell Biol. 205(4):591-606 (2014). doi:10.1083/jcb.201402066.
Rose, R. et al., "Ocular ascorbate transport and metabolism," A. Comp. Physiol., 100, 1991, 273-85.
Rothbauer, M. et al., "Exploitation of S-Layer Anisotropy: pH-Dependent Nanolayer Orientation for Cellular Micropatterning," Acs NANO, published online, 2013.
Sakai, T. et al., "Design and Fabrication of a High-Strength Hydrogel with Ideally Homogenous Network Structure from Tetrahedron-Like Macromonomers," Macromolecules, vol. 41, 2008, 5379-5384.
Sarrazin, S. et al. "Heparan sulfate proteoglycans." Cold Spring Harb. Perspect. Biol. 2011;3:a004952. doi: 10.1101/cshperspect.a004952.
Schindelin J., et al., "Fiji: an open-source platfonn for biological-image analysis," Nature Methods, vol. 9, pp. 676-682 (2012).
Schnell, U., et al. "Immunolabeling artifacts and the need for live-cell imaging." Nat. Methods 9, 152-158 (2012).
Scicchitano, M. S., et al. "Protein extraction of formalin-fixed, paraffin-embedded tissue enables robust proteomic profiles by mass spectrometry." J. Histochem. Cytochem. 57(9): 849-860 (2009). doi:10.1369/jhc.2009.953497.
Seifert, U. "Configurations of fluid membranes and vesicles." Adv. Phys. 46(1):13-137 (1997). doi:10.1080/00018739700101488.
Seneviratne, U., et al., "S-nitrosation of Proteins Relevant to Alzheimer's Disease During Early Stages of Neurodegeneration," PNAS, vol. 113, No. 15, Apr. 12, 2016, 4152-4157.
Shah, S., et al., "Single-Molecule RNA Detection at Depth Via Hybridization Chain Reaction and Tissue Hydrogel Embedding and Clearing," Jun. 24, 2016, published by the Company of Biologists, Ltd., http://dev.biologists.org/lookup/doi/10.1242/dev.138560.
"Shaner, N. C. et al., ""Improved monomeric red, orange and yellow fluorescent proteinsderived from *Discosoma* sp. red fluorescent protein,"" Nat. Biotechnol., 22, 2004, 1567-72."
Shaner, N. C. et al., "Improving the photostability of bright monomeric orange and red fluorescent proteins," Nat. Methods, 5, 2008, 545-51.
Shcherbakova, D. M., "An orange fluorescent protein with a large Stokes shift for single-excitation multicolor FCCS and FRET imaging," J. Am. Chem. Soc., 134, 2012, 7913-23.
Shcherbo, D. et al. "Far-red fluorescent tags for protein imaging in living tissues." Biochem. J. 418, 567-74 (2009).
Shen, K., et al. "Comparison of different buffers for protein extraction from formalin-fixed and paraffin-embedded tissue specimens." PLoS One 10(11): e0142650 (2015). doi:10.1371/journal.pone.0142650.
Shi, S. R., et al. "Antigen retrieval in formalin-fixed, paraffin-embedded tissues: An enhancement method for immunohistochemical staining based on microwave oven heating of tissue sections." J. Histochem. Cytochem. 39(6):741-8 (1991) doi:10.1177/39.6.1709656.
Sleytr, U. et al., "S-Layers Principles and Applications," FEMS Microbiology Rev., 2014, 1-42.
Sleytr, U. et al., "Heterologous Reattachment of Regular Arrays of Glycoproteins on Bacterial Surfaces," Nature, vol. 257, 1975, 400-401.
Sniegowski, J. A. et al., "Maturation efficiency, trypsin sensitivity, and optical properties of Arg96, Glu222, and Gly67 variants of green fluorescent protein," Biochem. Biophys. Res. Commun., 332, 2005, 657-63.
Steward, O. et al., "Compartmentalized synthesis and degradation of proteins in neurons," Neuron, vol. 40, 2003, 347-359.
Steward, O. et al., "Synaptic activation causes the mRNA for the leg Arc to localize selectively near activated postsynaptic sites on dendrites," Neuron, vol. 21, 1998, 741-751.
Strack, R., "Imaging Bigger is Better for Super-Resolution," Nature Methods, 12(13), Mar. 1, 2015, 169.
Subach, et al. "An Enhanced Monomeric Blue Fluorescent Protein with the High Chemical Stability of the Chromophore", PLoS One, 6, 2011, e28674.

(56) References Cited

OTHER PUBLICATIONS

Subach, F. V. et al., "Bright monomeric photoactivatable red fluorescent protein for two color super-resolution sptPALM of live cells," J. Am. Chem. Soc., 132, 2010, 6481-91.
Tanca, A. et al. "Comparability of differential proteomics data generated from paired archival fresh-frozen and formalin-fixed samples by GeLC-MS/MS and spectral counting." J. Proteomics 77:561-576 (2012). doi:10.1016/j.jprot.2012.09.033.
Tanca, A. et al. "Critical comparison of sample preparation strategies for shotgun proteomic analysis of formalin-fixed, paraffin-embedded samples: Insights from liver tissue." Clin. Proteomics 11:28 (2014). doi:10.1186/1559-0275-11-28.
Testagrossa et al. "Immunohistochemical expression of podocyte markers in the variants of focal segmental glomerulosclerosis." National Dial Transplant 28: 91-98 (2013).
Thevenaz, P., et al., "A pyramid approach to subpixel registration based on intensity," IEEE Trans. Image Process.7, 27-41 (1998).
Tillberg, P.W., et al. "Protein-Retention Expansion Microscopy of Cells and Tissues Labeled Using Standard Fluorescent Proteins and Antibodies," Nature Biotechnology, vol. 34, No. 9, Sep. 2016, 987-995.
Valenzuela, J. I. et al. "Diversifying the secretory routes in neurons." Frontiers in Neuroscience 9:358 (2015). doi:10.3389/fnins.2015.00358.
Van Meer, G., et al. "Membrane lipids: Where they are and how they behave." Nature Reviews Molecular Cell Biology 9(2): 112-124 (2008). doi:10.1038/nrm2330.
Van Vliet, et al., "The Biomechanics Toolbox: Experimental Approaches for Living Cells and Biomolecules," Acta Materialia 51: pp. 5881-5905, Aug. 23, 2003, [online], retrieved from the Internet, Oct. 23, 2015.
Vedaldi, A. et al. "VIfeat: an open and portable library of computer vision algorithms" in MM '10: Proceedings of the 18th ACM international conference on Multimedia, Oct. 2010 p. 1469-1472. https://doi.org/10.1145/1873951.1874249.
Wachter, R. M. et al., "Sensitivity of the yellow variant of green fluorescent protein to halides and nitrate," Curr. Biol, 9, 1999, R628-R629.
Wang, F. et al., "RNAscope: A novel in situ RNA analysis platform for formalin-fixed, paraffin-embedded tissues," Journal of Molecular Diagnostics, vol. 14(1), 2012, 22-29.
Wassie, A. T., et al. "Expansion microscopy: principles and uses in biological research." Nature Methods 16(1): 33-41 (2019). doi:10.1038/s41592-018-0219-4.
Weber, P. C., et al. "Structural origins of high-affinity biotin binding to streptavidin." Science 243(4887):85-88 (1989). doi:10.1126/science.2911722.
Wen, G. et al. "Evaluation of direct grafting strategies in Expansion Microscopy," BioRxiv preprint Jul. 8, 2019, doi: https://doi.org/10.1101/696039 (Jul. 8, 2019).
Wu, C. et al., "A method for the comprehensive proteomic analysis of membrane proteins," Nat. Biotechnol., 21, 2003, 532-8.
Wurm, C. A. et al. "Nanoscale distribution of mitochondrial import receptor Tom20 is adjusted to cellular conditions and exhibits an inner-cellular gradient." Proc. Natl. Acad. Sci. U. S. A. 108(33):13546-13551 (2011). doi:10.1073/pnas.1107553108.
Xu, J. et al., "Bioorthogonally cross-linked hydrogel network with precisely controlled disintegration time over a broad range," J. Am. Chem. Soc., vol. 136, No. 11, Mar. 19, 2014, 4105-4108.
Yan, B. X. et al. "Glycine residues provide flexibility for enzyme active sites." J. Biol. Chem. 272(6): 3190-4 (1997). doi: 10.1074/jbc.272.6.3190.
Yazici, I. et al., "Spatial Inhomogeneity in Poly(acrylic acid) Hydrogels," Polymer, vol. 46, 2005, 2595-2602.
Yu, C-C et al., "Expansion microscopy of C.elegans," ELIFE. [Online] DOI: 10.7554/elife.46249. Retrieved from the Internet:URL:https://elifesciences.org/articles/46249> [retrieved on Feb. 26, 2021], May 1, 2020, p. 125.

Zhang, D., et al., "Dynamic DNA nanotechnology using strand-displacement reactions," Nature Chemistry, vol. 3, pp. 103-113 (2011).
Zhang, R. et al., "Tools for GPCR Drug Discovery," Acta Pharmacologica Sinica, 33, 2012, 372-384.
Zhao, Y. et al. "Nanoscale imaging of clinical specimens using pathology-optimized expansion microscopy." Nat. Biotechnol. 35(8): 757-764 (2017). doi:10.1038/nbt.3892.
Zhou, C. et al., "Synthesis and characterization of well-defined PAA-PEG multiresponsive hydrogels by ATRP and click chemistry," RSC Adv., vol. 4, No. 97, Jan. 1, 2014, 54631-54640.
Zimmerman et al., "Adapting the stretched sample method from tissue profiling to imaging." Proteomics, 8, (2008), p. 3809-3815.
Zuiderveld, K. "Contrast Limited Adaptive Histogram Equalization." in Graphics Gems 474-485 (1994). doi:10.1016/b978-0-12-336156-1.50061-6.
Al, H. et al., "Exploration of new chromophore structures leads to the identification of improved blue fluorescent proteins," Biochemistry, 46, 2007, 5904-10.
Akhavan, A. et al., "Molecular Epizootiology of Rodent Leishmaniasis in a Hyperendemic Area of Iran," Iranian J Publ. Health, vol. 39, No. 1, 2010, 1-7.
Asano, S. M. et al., Expansion Microscopy: Protocols for Imaging Proteins and RNA in Cells and Tissues, Current Protocols in Cell Bio., vol. 80, No. 1, Online: DOI: 10.1002/cpcb.56. Retrieved from the Internet: URL:https://onlinelibrary.wiley.com/doi/fullxml/10.1002/cpcb.56> [retrieved on Feb. 26, 2021], Sep. 2, 2018.
Bates, M. et al., "Multicolor super-resolution imaging with photo-switchable fluorescent probes," Science, 317, 2007, 1749-1753.
Batish, M. et al., "Neuronal mRNAs Travel Singly into Dendrites," PNAS, vol. 109(12), 012, 4645-4650.
Beliveau, B. et al., "Versatile design and synthesis platform for visualizing genomes with Oligopaint FISH probes," PNAS, vol. 109(52): pfa, 2012, 21301-21306.
Bi, X. et al., "In situ-forming cross-linking hydrogel systems: chemistry and biomedical applications," In: 'Emerging Concepts in Analysis and Applications of Hydrogels', INTECH, Aug. 24, 2016, 131-158.
Bleckmann, J. et al., "Surface-Layer Lattices as Patterning Element for Multimeric Extremozymes," Small Journal, 2013, 1-8.
Bokman, S. H. et al. "Renaturation of Aequorea green-fluorescent protein." Biochem. Biophys. Res. Commun. 101, 1372-80 (1981).
Bossi, M. et al. "Multicolor far-field fluorescence nanoscopy through isolated detection of distinct molecular species." Nano Lett. 8, 2463-8 (2008).
Boutin, J. A. "Myristoylation." Cell. Signal, 9(1):15-35. (Jan. 1997) doi:10.1016/80898-6568(96)00100-3.
Breitwieser, A. et al., "Magnetic Beads Functionalized with Recombinant S-Layer Protein Exhibit High Human IgG-Binding and Anti-Fouling Properties," Current Topics in Peptide & Protein Research, vol. 17, 2016, 45-55.
Bruchez, M. et al., "Semiconductor nanocrystals as fluorescent biological labels," Science, vol. 281, 1998, Jun. 2013.
Buckley, P. et al., "Cytoplasmic Intron Sequence-Retaining Transcripts Can Be Dendritically Targeted via ID Element Retrotransposons," Neuron, vol. 69, 2011, 877-884.
Buenrostro, J. D. et al., AT AC-seq: A Method for Assaying Chromatin Accessibility Genome-Wide In 'Current Protocols in Molecular Biology,' Wiley, New York, NY, Jan. 5, 2015.
Bullock, G. R. "The current status of fixation for electron microscopy: A review." J. Microsc., 133: 1-15. (1984). doi:10.1111/j.1365-2818.1984.tb00458.x.
Buxbaum, A. et al., "Single-Actin mRNA Detection in Neurons Reveals a Mechanism for Regulating Its Translatability," Science, vol. 343, 2014, 419-422.
Cabili, M. et al., "Localization and abundance analysis of human lncRNAs at single-cell and single-molecule resolution," Genome Biology, vol. 16(20), 2015.
Cai, D., et al. "Improved tools for the Brainbow toolbox." Nat. Methods 10, 540-7 (2013).
Cajigas, I. et al., "The local transcriptome in the synaptic neuropil revealed by deep sequencing and high-resolution imaging," Neuron 74, 2012, 453-466.

(56) References Cited

OTHER PUBLICATIONS

Cao, W.,"DNA ligases and ligase-based technologies," Clinical and Applied Immunology Reviews, Elsevier, Amsterdam, NL, vol. 2, No. 1, Jan. 15, 2001, 33-43.

Carpenter, A. E. et al., "CellProfiler: image analysis software for identifying and quantifying cell phenotypes," Genome Biol., 7, 2006, R100.

Chang, et al. "Iterative expansion microscopy," Nature Methods, 14(6), (2017), p. 593-599, and supplemental info (4 pages, 11 pages total) (Year: 2017).

Chen et al., "Nanoscale imaging of RNA with expansion microscopy," 2016, Nature methods, 13, 679-684, (Year: 2016).

Chen et al. "Expansion microscopy," Science, Jan. 30, 2015, vol. 347, Issue 6221, pp. 543-548.

Chen, F. et al., "Supplementary Material for Expansion Microscopy", Science, 34 7(6221 ), Jan. 15, 2015, 543-548.

Chen, K. et al., "Spatially resolved, highly multiplexed RNA profiling in single cells," Science. vol. 348(6233), 2015, aaa6090-aaa6090.

Chen, X et al. [Supplementary material] "AT AC-see reveals the accessible genome by transposase-mediated imaging and sequencing," Nature Methods, vol. 13, No. 12, Oct. 17, 2016, 1813-1828.

Chen, X et al. "AT AC-see reveals the accessible genome by transposase-mediated imaging and sequencing," Nature Methods, vol. 13, No. 12, Oct. 17, 2016, 1813-1828.

Choi, H. et al., "Next-Generation in Situ Hybridization Chain Reaction: Higher Gain, Lower Cost, Greater Durability," ACS Nano 8(5), 2014, 4284-4294.

Choi, H. et al., "Programmable in situ amplification for multiplexed imaging of mRNA expression," Nature Biotechnology, 28(11), 2010, 1208-1212.

Chozinski, T. et al., "Expansion microscopy with conventional antibodies and fluorescent proteins," Nature Methods, vol. 13(6), 2016, 485-491.

Chu, J. et al., "Non-invasive intravital imaging of cellular differentiation with a bright redexcitable fluorescent protein," Nat. Methods, 11, 2014, 572-8.

Clemson, C. et al., "An architectural role for a nuclear noncoding RNA: NEAT1 RNA is Essential for the Structure of Paraspeckles" Mol Cell. Mar. 27, 2009;33(6):717-26. doi: 10.1016/j.molcel.2009.01.026.

Cochilla, A. J. et al. "Monitoring secretory membrane with FM1-43 flourescence." Annu. Rev. Neurosci. 22:1-10 (1999). doi:10.1146/annurev.neuro.22.1.1.

Cormack, B. P. et al., "FACS-optimized mutants of the green fluorescent protein (GFP)," Gene, 173, 1996, 33-8.

Invitrogen "Crosslinking and Photoactivatable Reagents," Chapter 5 in "Molecular Probes TM Handbook A Guide to Fluorescent Probes and Labeling Technologies", 11th Edition, 2010, 171-188.

Cubitt, A. B. et al., "Understanding structure-function relationships in the Aequorea victoria green fluorescent protein," Methods Cell Biol., 58, 1999, 19-30.

Danilczyk, U. G., et al. "Functional relationship between calreticulin, calnexin, and the endoplasmic reticulum luminal domain of calnexin." J. Biol. Chem. 275(17): 13089-13097 (2000). doi:10.1074/jbc.275.17.13089.

Dedecker, P. et al., "Localizer: fast, accurate, open-source, and modular software package for superresolution microscopy," J. Biomed. Opt., 17, 2012, 126008.

DiLorenzo, F. et al., "Nanostructural Heterogeneity in Polymer Networks and Gels, Polymer Chemistry," published on Jan. 5, 2015, vol. 6, pp. 5515-5528.

Duan, C. et al., "Application of antigen retrieval method in hMAM immunohistochemical staining of old paraffin-embedded specimens," Academy of Military Medical Sciences, vol. 38(12), Dec. 31, 2014, 965-967.

Edelstein, A. et al., "Computer control of microscopes using uManager," Curr. Protoc. Mol. Biol. Chapter 14, Unit 14.20, 2010.

English, A. R. et al. "Endoplasmic reticulum structure and interconnections with other organelles." Cold Spring Harbor Perspectives in Biology 2013;5:a013227. doi:10.1101/cshperspect.a013227.

English, B. P. et al., "A three-camera imaging microscope for high-speed single-molecule tracking and super-resolution imaging in living cells." Proc SPIE Int Soc Opt Eng. Aug. 21, 2015;9550:955008. doi: 10.1117/12.2190246.

Engreitz, J. et al., "The Xist lncRNA exploits three-dimensional genome architecture to spread across the X chromosome," Science 341, 2013, 1237973.

ThermoFisher Scientific "Epitope Recovery Methods for IHC", Nov. 7, 2015, pp. 1-2.

Femino, A. et al., "Visualization of Single RNA Transcripts in Situ," Science, vol. 280, 1998, 585-590.

Feng, G. et al., "Imaging neuronal subsets in transgenic mice expressing multiple spectral variants of GFP," Neuron, 28, 2000, 41-51.

Ferri A. "Expansion Microscopy: A New Approach to Microscopic Evaluation. (Master's thesis)." 2020 Retrieved from https://scholarcommons.sc.edu/etd/6034.

Caprette, "Experimental Biosciences: Resources for Introductory & Intermediate level laboratory courses" (2012), available online at https://www.ruf.rice.edu/~bioslabs/studies/sds-page/denature.html (Year: 2012).

Cho et al., "Expansion Microscopy" (2018), Journal of Microscopy, vol. 271, Issue 2: 123-128. (Year: 2018).

Alon, S. et al. Expansion sequencing: Spatially precise in situ transcriptomics in intact biological systems. Science 371, 481-+, doi:10.1126/science.aax2656 (2021).

Cahoon, C. K. et al. Superresolution expansion microscopy reveals the three-dimensional organization of the *Drosophila* synaptonemal complex. Proc Natl Acad Sci U S A 114, E6857-E6866, doi:10.1073/pnas.1705623114 (2017).

Campbell, K. R. et al. clonealign: statistical integration of independent single-cell RNA and DNA sequencing data from human cancers. Genome Biol 20, 54, doi:10.1186/s13059-019-1645-z (2019).

Chen, G. et al. Reactivity of functional groups on the protein surface: development of epoxide probes for protein labeling. J Am Chem Soc 125, 8130-8133, doi:10.1021/ja034287m (2003).

Cirillo, L. et al. UBAP2L forms distinct cores that act in nucleating stress granules upstream of G3BP1. Curr Biol 30, 698-707 e696, doi:10.1016/j.cub.2019.12.020 (2020).

Cote, A. et al. The spatial distributions of pre-mRNAs suggest post-transcriptional splicing of specific introns within endogenous genes. bioRxiv, doi:10.1101/2020.04.06.028092 (2020).

Cui, Y. et al. Fluctuation localization imaging-based fluorescence in situ hybridization (fliFISH) for accurate detection and counting of RNA copies in single cells. Nucleic Acids Res 46, e7, doi:10.1093/nar/gkx874 (2018).

Cui, Y. et al. Quantitative mapping of oxidative stress response to lithium cobalt oxide nanoparticles in single cells using multiplexed in situ gene expression analysis. Nano Lett 19, 1990-1997, doi:10.1021/acs.nanolett.8b05172 (2019).

Decarreau, J. et al. Corrigendum: The tetrameric kinesin Kif25 suppresses pre-mitotic centrosome separation to establish proper spindle orientation. Nat Cell Biol 19, 740, doi:10.1038/ncb3546 (2017).

Decarreau, J. et al. The tetrameric kinesin Kif25 suppresses pre-mitotic centrosome separation to establish proper spindle orientation. Nat Cell Biol 19, 384-390, doi: 10.1038/ncb3486 (2017).

Eirew, P. et al. Dynamics of genomic clones in breast cancer patient xenografts at single-cell resolution. Nature 518, 422-426, doi:10.1038/nature13952 (2015).

Falahati, H. et al., Thermodynamically driven assemblies and liquid-liquid phase separations in biology. Soft Matter 15, 1135-1154, doi: 10.1039/c8sm02285b (2019).

Fecher, C. et al. Cell-type-specific profiling of brain mitochondria reveals functional and molecular diversity. Nat Neurosci 22(10), 1731-1742 doi:10.1038/s41593-019-0479-z (2019).

Gambarotto, D. et al. Imaging cellular ultrastructures using expansion microscopy (U-ExM). Nat Methods 16, 71-74, doi:10.1038/s41592-018-0238-1 (2019).

(56) References Cited

OTHER PUBLICATIONS

Gao, M. et al. Expansion stimulated emission depletion microscopy (ExSTED). ACS Nano 12, 4178-4185, doi:10.1021/acsnano.8b00776 (2018).

Gao, R. et al. A highly homogeneous polymer composed of tetrahedron-like monomers for high-isotropy expansion microscopy. Nat Nanotechnol 16, 698-707, doi:10.1038/s41565-021-00875-7 (2021).

Gao, R. et al. Cortical column and whole-brain imaging with molecular contrast and nanoscale resolution. Science 363 (6424), doi:10.1126/science.aau8302 (2019).

Hafner, A. S. et al., Local protein synthesis is a ubiquitous feature of neuronal pre- and postsynaptic compartments. Science 364, doi:10.1126/science.aau3644 (2019).

Halpern, A. R. et al., Hybrid structured illumination expansion microscopy reveals microbial cytoskeleton organization. ACS Nano 11, 12677-12686, doi:10.1021/acsnano.7b07200 (2017).

Hansen, M., Lee, S. J., Cassady, J. M. & Hurley, L. H. Molecular details of the structure of a psorospermin-DNA covalent/intercalation complex and associated DNA sequence selectivity. J Am Chem Soc 118, 5553-5561 (1996).

He, J. et al. Prevalent presence of periodic actin-spectrin-based membrane skeleton in a broad range of neuronal cell types and animal species. Proc Natl Acad Sci U S A 113, 6029-6034, doi:10.1073/pnas.1605707113 (2016).

Invitrogen Corporation, "Proteinase K (solution), RNA Grade", Cat. No. 25530-049, rev. date: Aug. 25, 2008, 2 pages, accessed from https://www.thermofisher.com/document-connect/document-connect.html?url=https://assets.thermofisher.com/TFS-Assets%2FLSG%2Fmanuals%2Fproteinasek_solution_man.pdf (2008).

Kao, P. et al., Transcriptional activation of Arabidopsis zygotes is required for initial cell divisions. Sci Rep 9, 17159, doi:10.1038/s41598-019-53704-2 (2019).

Karagiannis, E. D. et al. Expansion microscopy of lipid membranes. bioRxiv, 829903, doi:10.1101/829903 (2019).

Keenan et al., "An automated machine vision system for the histological grading of cervical intraepithelial neoplasia (CIN)," Journal of Pathology, J Pathol 2000; 192: pp. 351-362.

Koppers, M. et al. Receptor-specific interactome as a hub for rapid cue-induced selective translation in axons. Elife 8, 1-27 doi:10.7554/eLife.48718 (2019).

Kumar, A. et al. Influenza virus exploits tunneling nanotubes for cell-to-cell spread. Sci Rep 7, 1-14, 40360, doi:10.1038/srep40360 (2017).

Kunz, T. C. et al., Using Expansion Microscopy to Visualize and Characterize the Morphology of Mitochondrial Cristae. Front Cell Dev Biol 8, 617, doi:10.3389/fcell.2020.00617 (2020).

Li, R. et al., Expansion enhanced nanoscopy. Nanoscale 10, 17552-17556, doi:10.1039/c8nr04267e (2018).

Lim, Y. et al. Mechanically resolved imaging of bacteria using expansion microscopy. PLoS Biol 17, e3000268, doi:10.1371/journal.pbio.3000268 (2019).

Martinez, G. F. et al. Quantitative expansion microscopy for the characterization of the spectrin periodic skeleton of axons using fluorescence microscopy. Sci Rep 10, 2917, doi: 10.1038/s41598-020-59856-w (2020).

Mosca, T. J. et al., Presynaptic LRP4 promotes synapse number and function of excitatory CNS neurons. Elife 6, doi:10.7554/eLife.27347 (2017).

M'Saad, O. et al., Light microscopy of proteins in their ultrastructural context. Nat Commun 11, 3850, doi:10.1038/s41467-020-17523-8 (2020).

Park, Y. G et al. Protection of tissue physicochemical properties using polyfunctional crosslinkers. Nat Biotechnol 37, 73-83, doi:10.1038/nbt.4281 (2019).

Richter, S. et al. Clerocidin alkylates DNA through its epoxide function: evidence for a fine tuned mechanism of action. Nucleic Acids Res 31, 5149-5156, doi:10.1093/nar/gkg696 (2003).

Sahl, S. J. et al., Fluorescence nanoscopy in cell biology. Nat Rev Mol Cell Biol 18(11), 685-701, doi:10.1038/nrm.2017.71 (2017).

Sarkar, D. et al. Expansion revealing: decrowding proteins to unmask invisible brain nanostructures. bioRxiv, doi:10.1101/2020.08.29.273540 (2020).

Shen, F. Y. et al. Light microscopy based approach for mapping connectivity with molecular specificity. Nat Commun 11, 4632, doi: 10.1038/s41467-020-18422-8 (2020).

Shurer, C. R. et al. Physical principles of membrane shape regulation by the glycocalyx. Cell 177, 1757-1770 e1721, doi:10.1016/j.cell.2019.04.017 (2019).

Sidenstein, S. C. et al. Multicolour multilevel STED nanoscopy of actin/spectrin organization at synapses. Sci Rep 6, 26725, doi:10.1038/srep26725 (2016).

So, C. et al. A liquid-like spindle domain promotes acentrosomal spindle assembly in mammalian oocytes. Science 364, doi:10.1126/science.aat9557 (2019).

Suofu, Y. et al. Dual role of mitochondria in producing melatonin and driving GPCR signaling to block cytochrome c release. Proc Natl Acad Sci U S A 114, E7997-E8006, doi:10.1073/pnas.1705768114 (2017).

Thevathasan, J. V. et al. Nuclear pores as versatile reference standards for quantitative superresolution microscopy. Nat Methods 16, 1045-1053, doi: 10.1038/s41592-019-0574-9 (2019).

Tillberg, P. W. et al. Expansion microscopy: scalable and convenient super-resolution microscopy. Annu Rev Cell Dev Biol 35, 683-701, doi:10.1146/annurev-cellbio-100818-125320 (2019).

Truckenbrodt et al., A practical guide to optimization in X10 expansion microscopy. Nat Protoc 14, 832-863, doi:10.1038/s41596-018-0117-3 (2019).

Valdes, P. A. et al. Decrowding expansion pathology: unmasking previously invisible nanostructures and cells in intact human brain pathology specimens. bioRxiv, doi:10.1101/2021.12.05.471271 (2021).

Wang, G. et al., Multiplexed imaging of high-density libraries of RNAs with MERFISH and expansion microscopy. Sci Rep 8(4847), 1-13 doi:10.1038/s41598-018-22297-7 (2018).

Wang, Y. et al. EASI-FISH for thick tissue defines lateral hypothalamus spatio-molecular organization. Cell 184, 6361-6377 e6324, doi:10.1016/j.cell.2021.11.024 (2021).

Xu, H. et al. Molecular organization of mammalian meiotic chromosome axis revealed by expansion STORM microscopy. Proc Natl Acad Sci U S A 116, 18423-18428, doi:10.1073/pnas.1902440116 (2019).

Xu, K. et al., Actin, spectrin, and associated proteins form a periodic cytoskeletal structure in axons. Science 339, 452-456, doi:10.1126/science.1232251 (2013).

Bensimon, A. et al., "Alignment and Sensitive Detection of DNA by a Moving Interface." Alignment and Sensitive Detection of DNA by a Moving Interface.

Cheeseman, Kevin, et al. "A Diagnostic Genetic Test for the Physical Mapping of Germline Rearrangements of the Susceptibility Breast Cancer Genes BRCA1 and BRCA2." Human Mutation, vol. 33, No. 6, 998-1009, 2012.

Diggle MA et al., A novel method for preparing single-stranded DNA for pyrosequencing, 2003, Molecular Biotechnology, 24(2):221-224.

Dong, Huimin et al. "Preparation of photodeformable azobenzene polymer fibers by post-crosslinking strategy: Understanding the structure-property relationship", European Polymer Journal, Pergamon Pressltd Oxford, GB, vol. 135, Jul. 10, 2020 (Jul. 10, 2020), XP086242455, ISSN: 0014-3057, DOI:10.1016/J.EURPOLYMJ.2020.109863.

Gad, Sophie, et al. "Identification of a large rearrangement of the BRCA1 gene using colour bar code on combed DNA in an American breast/ovarian cancer family previously studied by direct sequencing." F. Med Genet 2001; 38:388-392.

Gann et al., Development of a nuclear morphometric signature for prostate cancer risk in negative biopsies, PLoS One, Jul. 26, 2013, pp. 1-9, doi: 10.1371/journal.pone.0069457.

Hodson, Robert E. et al. "In Situ PCR for Visualization of Microscale Distribution of Specific Genes and Gene Products in Prokaryotic Communities." Applied and Environmental Microbiology, Nov. 1995, p. 4074-4082.

(56) References Cited

OTHER PUBLICATIONS

Jain, Miten et al. "Nanopore sequencing and assembly of a human genome with ultra-long reads." Nature Biotechnology, vol. 36, No. 4, Apr. 2018.

Kaykov, A., et al. "Molecular Combing of Single DNA Molecules on the 10 Megabase Scale." Sci. Rep. 6, 19636, 2016, p. 1-9.

Kondo, N. et al. "DNA Damage Induced by Alkylating Agents and Repair Pathways." Journal of Nucleic Acids, vol. 2010, Article ID 543531, 7 pages.

Larsson, Chatarina et al. "In situ genotyping individual DNA molecules by target-primed rolling-circle amplification of padlock probes." Nature Methods, vol. 1, No. 3, Dec. 2004.

Lunzer, Markus et al. "A Modular Approach to Sensitized Two-Photon Patterning of Photodegradable Hydrogels", Angewandte Chemie, Wiley—V CH Verlaggmbh & Co. KGAA, DE, vol. 130, No. 46, (Oct. 18, 2018), pp. 15342-15347, XP071375228, ISSN: 0044-8249, DOI:10.1002/ANGE.201808908.

Marie, R. et al. "Concentrating and labeling genomic DNA in a nanofluidic array." Nanoscale. 10 (2018), pp. 1376-1382.

Maxam, A. M., and Gilbert W., "A new method for sequencing DNA." Proc. Natl. Acad. Sci. U.S.A., 74, 560-564, 1977.

Nyren, Pal, et al. "Solid Phase DNA Minisequencing by an Enzymatic Luminometric Inorganic Pyrophosphate Detection Assay." Analytical Biochemistry 208, 171-175 (1993).

Rapp, Teresa L. et al. "Visible Light-Responsive Dynamic Biomaterials: Going Deeper and Triggering More", Advanced Healthcare Materials, Wiley—V CH Verlag Gmbh & Co. KGAA, DE, vol. 9, No. 7, Feb. 25, 2020, p. n/a, XP072463096, ISSN: 2192-2640, DOI:10.1002/ADHM.201901553.

Schirmer, M., et al. "Insight into biases and sequencing errors for amplicon sequencing with the Illumina MiSeq platform." Nucleic Acids Research, vol. 43, Issue 6, Mar. 31, 2015, e37, pp. 1-16.

Schonhuber, Wilhelm, et al. "Improved Sensitivity of Whole-Cell Hybridization by the Combination of Horseradish Peroxidase-Labeled Oligonucleotides and Tyramide Signal Amplification." Applied and Environmental Microbiology, Aug. 1997, p. 3268-3273.

Shendure, J., et al. "DNA sequencing at 40: past, present, and future." Nature 2017, Oct. 19;550(7676): 345-353.

Sikdar, Partha et al. "Recent advances in the synthesis of smart hydrogels", Materials Advances, vol. 2, No. 14, Jan. 1, 2021, pp. 4532-4573, XP093067739,DOI: 10.1039/D1MA00193K.

Singh, Anirudha et al. "Photomodulation of Cellular Gene Expression in Hydrogels", ACS Macro Letters, vol. 2, No. 3, (Mar. 8, 2013), pp. 269-272, XP093109803, ISSN: 2161-1653, DOI: 10.1021/mz300059lm.

Stankova, Helena, et al. "BioNano genome mapping of individual chromosomes supports physical mapping and sequence assembly in complex plant genomes." Plant Biotechnology Journal (2016) 14, pp. 1523-1531 doi: 10.1111/pbi.12513.

Strick, T., et al. "Twisting and stretching single DNA molecules." Progress in Biophysics & Molecular Biology 74 (2000) 115-140.

Ueda H.R., et al. "Tissue clearing and its applications in neuroscience." Nature Reviews, Neuroscience, vol. 21, Feb. 2020.

Varapula et al., A micropatterned substrate for on-surface enzymatic labelling of linearized long DNA molecules, 2019, Scientific Reports, 9, 15059.

Wages JM, Polymerase Chain Reaction, 2005, Encyclopedia of Analytical Science, (2): 243-250.

Wang et al., Detection and classification of thyroid follicular lesions based on nuclear structure from histopathology images, Cytometry A May 2010, 77(5):485-94, doi: 10.1002/cyto.a.20853. PMID: 20099247; PMCID: PMC3010854.

Wang, X., et al., "Characterization of denaturation and renaturation of DNA for DNA hybridization." Environ. Health Toxicol, 29, e2014007, 2014.

Yanagawa, Fumiki et al. "Activated-Ester-Type Photocleavable Crosslinker for Preparation of Photodegradable Hydrogels Using a Two-Component Mixing Reaction", Advanced Healthcare Materials, Wiley—V CH Verlag Gmbh & Co. KGAA, DE, vol. 4, No. 2, (Aug. 13, 2014), pp. 246-254, XP072465709, ISSN: 2192-2640, DOI:10.1002/ADHM.201400180.

Akhmetzhan, A., et al. "A short review on the N, N-Dimethylacrylamide-based hydrogels." Gels 7.4 (2021): 234.

Cipriano, B.H., et al. "Superabsorbent hydrogels that are robust and highly stretchable." Macromolecules 47.13 (2014): 4445-4452.

Klimas, A., et al. "Magnify is a universal molecular anchoring strategy for expansion microscopy." Nature biotechnology 41.6 (2023): 858-869.

Neely, R.K. et al., "Optical mapping of DNA: Single-molecule-based methods for mapping genomes." Biopolymers 95.5 (2011): 298-311.

Rueda, J.C., et al. "Synthesis and characterization of stiff, self-crosslinked thermoresponsive DMAA hydrogels." Polymers 12.6 (2020): 1401.

Truckenbrodt, S., et al. "X10 expansion microscopy enables 25-nm resolution on conventional microscopes." EMBO reports 19.9 (2018): e45836.

* cited by examiner

MEMBRANE PROBES FOR EXPANSION MICROSCOPY

RELATED APPLICATION

This application claims the benefit of U.S. Provisional Application No. 62/930,938, filed on Nov. 5, 2019. The entire teachings of the above application are incorporated herein by reference.

GOVERNMENT SUPPORT

This invention was made with Government support under Grant No. NS087724, awarded by the National Institutes of Health and under Grant No. W911NF-15-1-0548, awarded by the Army Research Office. The Government has certain rights in the invention.

BACKGROUND OF THE INVENTION

As previously described in, for example, WO 2015/127183 (incorporated herein by reference), expansion microscopy (ExM) physically magnifies biological specimens by covalently anchoring biomolecules or labels to a swellable polymer network (typically sodium polyacrylate) synthesized in situ throughout the specimen. Following tissue softening and solvent exchange, the hydrogel-specimen composite expands isotropically, typically to a physical magnification of ~4.5× in linear dimension. The net result is that biomolecules or labels that are initially localized within the diffraction limit of a traditional optical microscope can now be separated in space to distances far enough that they can be resolved on ordinary microscopes.

Lipids are fundamental building blocks of cells and their organelles, yet nanoscale resolution imaging of lipids has been largely limited to electron microscopy techniques. Traditional fluorescent membrane labeling probes (i.e., DiI and DiO) consist of long hydrophobic chains bearing fluorophores[8], which preferentially localize to and diffuse within membranes[9]. Recent iterations of such molecules (i.e., FM1-43FX[10] and mCLING[11]) also include hydrophilic moieties, like primary amines, to permit them to diffuse more freely in three dimensions throughout tissues prior to reaching their membrane targets. However, such probes are not compatible with ExM.

Thus, there is a need for membrane labeling probes that are compatible with ExM chemistry and can achieve dense enough membrane coverage to support nanoscale resolution imaging and allow continuous tracing of membraneous structures.

REFERENCE TO AN ELECTRONIC SEQUENCE LISTING

The contents of the electronic sequence listing (sequencelistingst25.txt; Size: 719 bytes; Date of Creation: Oct. 24, 2024) is herein incorporated by reference in its entirety.

SUMMARY OF THE INVENTION

The present invention provides compositions and methods that allow lipid membranes to be imaged optically at nanoscale resolution via a lipid-optimized form of expansion microscopy, also referred to as membrane expansion microscopy (mExM). mExM, via a post-expansion antibody labeling protocol, enables protein-lipid relationships to be imaged in organelles such as mitochondria, the endoplasmic reticulum, the nuclear membrane, and the Golgi apparatus. mExM may be of use in a variety of biological contexts, including the study of cell-cell interactions, intracellular transport, and neural connectomics.

In embodiments, the invention provides a membrane labeling probe comprising the Formula A-B-C-D, wherein A is a hydrophobic group, B is a linker, C is a polymer anchorable group, and D is a label binder.

In embodiments, the invention provides a method for enlarging a sample of interest, the method comprising the steps of: contacting the sample with the membrane labeling probe according to the invention; embedding the sample in a swellable material; subjecting the sample to a disruption of the endogenous physical structure of the sample; swelling the swellable material resulting in an enlargement of the sample;

BRIEF DESCRIPTION OF THE DRAWINGS

FIG. 1A shows tissue perfused and fixed with cold 4% PFA and 0.1% glutaraldehyde is sliced. Each tissue slice is incubated with 100 μM of pGk5b membrane label (chemical structure, lower left) in PBS at 4° C. overnight. The tissue is gelled following the established proExM protocol. If only membrane labeling is required, downstream processing of the tissue is similar to the already published proExM method[3]: the tissue is homogenized with proteinase K and labeled with fluorescent streptavidin (top row). The membrane labeling probe is not digested during proteinase K treatment because it is composed of D-amino acids. To incorporate antibody labeling, we developed a post-expansion antibody labeling technique (bottom row). In that case, the gelled tissue is thermally processed and expanded in a fixation reversal buffer, washed, and labeled with antibodies prior to the fluorescent labeling of pGk5b with streptavidin. FIG. 1B shows the labeling efficacy of the membrane labeling probe to label membranes with electron microscopy. 100 μM of pGk5 (with azide instead of biotin) was applied to 200 μm thick tissue slices from a mouse brain perfused with 4% PFA and 0.1% glutaraldehyde at 4° C., labelled with lipids for 2 days at 4° C., and labelled with 0.8 nm undecagold gold nanoparticles conjugated to dibenzocyclooctyne. The tissue was post-fixed in 2% glutaraldehyde, embedded in resin, counter-labeled with osmium tetraoxide and imaged. When labeling membranes with the palmitoylated version of the probe, the staining is dominated by the gold nanoparticles which overlap with osmium. The osmium staining (less contrast than the nanoparticles) becomes apparent when the tissue is labeled with the farnesylated probe, which exhibits less membrane coverage than the palmitoylated one (FIG. 4). Scale bars: 10 μm for the low-resolution images, 1 μm for the high-resolution insets. (c) Tissue labeled with pGk5b and unexpanded (i, zoomed out; iii, zoomed in) and post-expansion (ii, zoomed out; iv, zoomed in). All images were acquired with an Andor spinning-disk (CSU-W1 Tokogawa) confocal system on a Nikon Eclipse Ti-E inverted microscope body with a 40× 1.15 NA water-immersion objective. Either when observing a collection of neurons (i anA and ii) or a single neuron (iii and iv), mExM yields more detail than can be observed in the unexpanded sample, even using the novel lipid stain. The unexpanded images are sized to match the biological scale of the expanded sample. Scale bars represented in pre-expansion units: 10 μm for (i) and (ii), and 5 μm for (iii) and (iv).

FIG. 2A mExM enables the labeling of membranes in thick pieces of mouse brain tissue. Here shown are six serial sections from a 3D image stack taken with a confocal spinning disk microscope. Axons can be identified by their high contrast due to the increased concentration of lipids in myelin (details shows with red arrows). FIG. 2B mExM processed tissue imaged with light-sheet microscopy. Scale bars represented in pre-expansion units: 10 µm.

DETAILED DESCRIPTION OF THE INVENTION

Figures 1A, 1B, 1C:
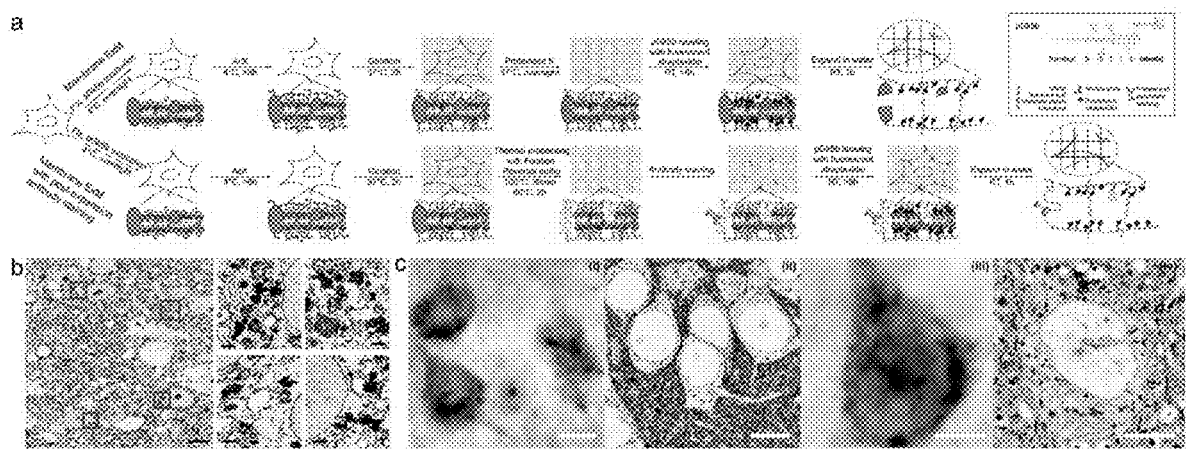
FIG. 1A through 1C. Membrane expansion microscopy (mExM) workflow and validation.

As used herein and in the appended claims, the singular forms "a", "an", and "the" are defined to mean "one or more" and include the plural unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The present invention provides compositions and methods that allow lipid membranes to be imaged optically at nanoscale resolution via a lipid-optimized form of expansion microscopy, also referred to as membrane expansion microscopy (mExM). mExM, via a post-expansion antibody labeling protocol, enables protein-lipid relationships to be imaged in organelles such as mitochondria, the endoplasmic reticulum, the nuclear membrane, and the Golgi apparatus. mExM may be of use in a variety of biological contexts, including the study of cell-cell interactions, intracellular transport, and neural connectomics.

In one embodiment, the invention provides a membrane labeling probe comprising the formula A-B-C-D, wherein A is an hydrophobic group, B is a linker, C is a polymer anchorable group, and D is a label binder. The membrane label probe of the invention is characterized in that the probe has amphiphilicity, a chemical handle, and a polymer-anchorable handle.

The hydrophobic group is provided to support both lipid membrane intercalation and diffusion in 3D tissues. Common hydrophobic substances are soaps, detergents and lipoproteins In embodiments, the hydrophobic groups is tween, an aliphatic group, an alkane group, or a fatty acid group. In embodiments the hydrophobic group is a fatty acid group. In embodiments, the hydrophobic group is palmitoyl.

In embodiments, linker is a bi-functional linker wherein the bi-functional linker comprises a moiety that will react the terminal portion of A and a moiety that will react with the terminal portion of C. In embodiments the linker has limited branching. In embodiments, the linker is linear. The linker acts to provide a hinge between the polymer and the lipid membrane.

In embodiments, the linker is a hetero-bifunctional crosslinker. Hetero-bifunctional crosslinkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation.

In embodiments, the linker can be a citrate, a fumarate, an ester, or an amino acid. In embodiments, the linker is an amino acid. In embodiments, the amino acid is glycine.

The polymer-anchorable handle provides for binding the membrane labeling probe to the polymer matrix (also referred to herein as "swellable material"), to allow expansion. The polymer anchorable group is characterized by 1 or more moieties which chemically react with moieties on the swellable material. In embodiments, the polymer anchorable group is 1 or more amino acids. In embodiments, the amino acids are the same or different. In embodiments, the amino acids are the same. In embodiments, the amino acids are different. In embodiments, the amino acids are lysine.

As shown in FIG. 1A (lower left), in some embodiments the membrane labeling probe comprises a chain of amino acids. In some embodiments, the chain of amino acids comprises amino acids having primary amines on their side chains. In some embodiments, the chain of amino acids comprises lysines, which contain primary amines on their side chains that could serve as sites for binding to a polymer-anchorable handle. The amines are also positively charged, which can help promote interactions with negatively charged membranes.

In embodiments, the membrane labeling probe comprises from about 2 to about 10 lysines. In embodiments, the membrane labeling probe comprises from about 3 to about 6 lysines. the membrane labeling probe comprises about 5 lysines.

In embodiments, to assist with lipid membrane intercalation, a lipid tail can be included on the amine terminus of the lysine chain, with a glycine in between to provide mechanical flexibility.

In embodiments, the size of the label is limited to ~1 kDa, to allow fast diffusion throughout tissue and dense labeling of membranes.

In embodiments the lysines can be D-lysines, rather than the biologically typical L-lysines. D-lysines may help to minimize degradation during the step of disruption of the endogenous biological molecules or the physical structure of the sample.

The polymer anchorable group may be, for example, acrylamide modified and therefore may be covalently fixed within a swellable material. As used herein, the term "acrylamide modified" in reference to polymer anchorable group means that the polymer anchorable group has an acrylamide moiety.

In one embodiment, the polymer anchorable group is treated with a succinimidyl ester of 6-((acryloyl)amino) hexanoic acid (acryloyl-X, SE; abbreviated "AcX"; Life Technologies) Treatment with AcX modifies amines on proteins with an acrylamide functional group. The acrylamide functional groups allows for proteins to be anchored to the swellable polymer as it is synthesized in situ.

The label binder provides for chemoselective conjugation of a fluorophore following the formation of the expandable hydrogel network. This allows for the molecular weight of the membrane labeling probe to be kept as small as possible to facilitate diffusion.

In one embodiment, label binder can be labeled or tagged with a detectable label. The detectable label can be selective for a specific target (e.g., a biomarker or class of molecule), as can be accomplished with an antibody or other target specific binder. The detectable label may comprise a visible component, as is typical of a dye or fluorescent molecule; however any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis. The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample.

In embodiments, a label binder is introduced to the carboxy terminus of the terminal polymer anchorable group. In embodiments, the label binder is biotin. Biotin can react with one of the four binding sites of a fluorescently labeled streptavidin administered later. The remaining active sites of the streptavidin can then be reacted with further biotinylated fluorophores to amplify the brightness manyfold.

As used herein, the term "attach" or "attached" refers to both covalent interactions and noncovalent interactions. The term "attach" may be used interchangeably herein with the terms, "anchor(ed)", affix(ed), link(ed) and immobilize(d).

As used herein, the term "sample of interest" generally refers to, but is not limited to, a biological, chemical or biochemical sample. In one embodiment, the sample of interest includes, but is not limited to, a tissue sample, a cell, or any components thereof.

A sample of interest is used herein in a broad sense and is intended to include sources that contain biomolecules and can be fixed. Exemplary tissue samples include, but are not limited to liver, spleen, kidney, lung, intestine, thymus, colon, tonsil, testis, skin, brain, heart, muscle and pancreas tissue. Other exemplary tissue samples include, but are not limited to, biopsies, bone marrow samples, organ samples, skin fragments and organisms. Materials obtained from clinical or forensic settings are also within the intended meaning of the term tissue sample. In one embodiment, the sample is derived from a human, animal or plant. In one embodiment, samples are human. The sample can be obtained, for example, from autopsy, biopsy or from surgery. It can be a solid tissue such as, for example, parenchyme, connective or fatty tissue, heart or skeletal muscle, smooth muscle, skin, brain, nerve, kidney, liver, spleen, breast, carcinoma (e.g. bowel, nasopharynx, breast, lung, stomach etc.), cartilage, lymphoma, meningioma, placenta, prostate, thymus, tonsil, umbilical cord or uterus. The tissue can be a tumor (benign or malignant), cancerous or precancerous tissue. The sample can be obtained from an animal or human subject affected by disease or other pathology or suspected of same (normal or diseased), or considered normal or healthy. As used herein, the term "tissue sample" explicitly excludes cell-free samples, for example cell extracts, wherein cytoplasmic and/or nuclear components from cells are isolated.

Tissue samples suitable for use with the methods and systems described herein generally include any type of tissue samples collected from living or dead subjects, such as, e.g., biopsy specimens and autopsy specimens. Tissue samples may be collected and processed using the methods and systems described herein and subjected to microscopic analysis immediately following processing or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human brain tissue samples, may be processed as described above and cleared to remove a plurality of cellular components, such as, e.g., lipids, and then stored for future analysis.

Tissues that have been preserved, or fixed, contain a variety of chemical modifications that can reduce the detectability of proteins in biomedical procedures. In some embodiments, the methods and systems described herein may be used to analyze a previously-preserved or stored tissue sample. Previously preserved tissue samples include, for example, clinical samples used in pathology including formalin-fixed paraffin-embedded (FFPE), hematoxylin and eosin (H&E)-stained, and/or fresh frozen tissue samples. If the previously preserved sample has a coverslip, the coverslip should be removed. The sample is treated to remove the mounting medium. Such methods for removing the mounting medium are well known in the art. For example, treating the sample with xylene to remove paraffin or other hydrophobic mounting medium.

Alternatively, if the sample is mounted in a water-based mounting medium, the sample is treated with water. The sample is then rehydrated and subjected to antigen-retrieval. The term "antigen retrieval" refers to any technique in which the masking of an epitope is reversed and epitope-antibody binding is restored such as, but not limited to, enzyme induced epitope retrieval, heat induced epitope retrieval (HIER), or proteolytic induced epitope retrieval (PIER). For example, the antigen retrieval treatment can be performed in a 10 mM sodium citrate buffer as well as the commercially available Target Retrieval Solution (DakoCytomation) or such.

As used herein, the terms "swellable material" and "swellable polymer" are used interchangeably and generally refers to a material that expands when contacted with a liquid, such as water or other solvent. Additionally or alternatively, the swellable material can be expanded by any other means known to one of skill in the art. In some embodiments, the swellable material uniformly expands in three dimensions. Additionally or alternatively, the material is transparent such that, upon expansion, light can pass through the sample. The first swellable material and the second swellable material may be the same or different swellable materials.

In one embodiment, the swellable material is formed in situ from precursors thereof. Embedding the sample in the swellable material comprises permeating the sample with a composition comprising one or more precursors thereof throughout the sample and polymerizing and/or crosslinking the monomers or precursors to form the swellable material. In this manner the sample of interest is embedded in the swellable material.

In one embodiment, the sample of interest and each iteratively enlarged sample is permeated with one or more monomers or precursors or a solution comprising one or more monomers or precursors which are then reacted to form a swellable or non-swellable material depending on what step of the method is being performed.

By "precursors of a swellable material" it is meant hydrophilic monomers, prepolymers, or polymers that can be crosslinked, or "polymerized", to form a three-dimensional (3D) hydrogel network. Precursors can also comprise polymerization initiators and crosslinkers.

In one embodiment the swellable material is a polyelectrolyte. In one embodiment, the swellable material is polyacrylate or polyacrylamide and copolymers or crosslinked copolymers thereof.

In some embodiments, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides).

In one embodiment, the precursor of the swellable material comprises at least one polyelectrolyte monomer and a covalent crosslinker. In one embodiment, the swellable material is a hydrogel. In one embodiment, the hydrogel is a polyacrylate hydrogel. In one embodiment, the precursor of the swellable material comprises acrylate, acrylamide, and a crosslinker selected from N,N-methylenebisacrylamide (BIS), N,N'-(1,2-Dihydroxythylene)bisacryalmide) (DHEBA); and N,N'-Bis(acryloyl)cystamine (BAC).

The precursors of the swellable polymer may be delivered to the biological specimen by any convenient method including, but not limited to, permeating, perfusing, infusing, soaking, adding or other intermixing the sample with the precursors of swellable material. In this manner, the biological specimen is saturated with precursors of the swellable material, which flow between and around biomolecules throughout the specimen.

Following permeating the specimen, the swellable polymer precursors are polymerized, i.e., covalently or physically crosslinked, to form a polymer network. The polymer network is formed within and throughout the specimen. In this manner, the biological specimen is saturated with the swellable material, which flow between and around biomolecules throughout the specimen.

Polymerization may be by any method including, but not limited to, thermal crosslinking, chemical crosslinking, physical crosslinking, ionic crosslinking, photo-crosslinking, irradiative crosslinking (e.g., x-ray, electron beam), and the like, and may be selected based on the type of hydrogel used and knowledge in the art. In one embodiment, the polymer is a hydrogel. Once polymerized, a polymer-embedded biological specimen is formed.

In one embodiment, the swellable polymer is polyacrylate and copolymers or crosslinked copolymers thereof. For example, if the biological sample is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacryalmide), and (DHEBA) N,N'-Bis(acryloyl)cystamine (BAC), are perfused throughout the sample.

In one embodiment, the swellable material is a swellable polymer or hydrogel. The hydrogel may be a polyelectrolyte hydrogel. The polyelectrolyte may be a polyacrylate.

By embedding a specimen in a swellable polymer that physically supports the ultrastructure of the specimen this technology preserves the biomolecules (e.g., proteins, small peptides, small molecules, and nucleic acids in the specimen) in their three-dimensional distribution, secured by the polymer network. By bypassing destructive sectioning of the specimen, subcellular structures may be analyzed. In addition, the specimen can be iteratively stained, unstained, and restrained with other reagents for comprehensive analysis.

In some embodiments, native proteins anchored to the swellable polymer perfused throughout the sample as described herein can retain epitope functionality and be labeled post-expansion if the nonspecific proteolysis of ExM is replaced with modified post-gelation homogenization treatments. Such approaches may overcome the limitations inherent to delivering antibodies in the crowded environment of native tissue.

Following anchoring, the sample is subjected to a disruption of the underlying network of biological molecules, leaving the tags of interest (e.g., the fluorescent dye molecules) intact and anchored to the gel. In this way, the mechanical properties of the swellable material-sample complex are rendered more spatially uniform, allowing isotropic expansion with minimal artifacts.

In one embodiment, the sample is anchored to the swellable material before expansion. This can be accomplished by chemically crosslinking the polymer anchorable group of the membrane labeling probe with the swellable material, such as during or after the polymerization or in situ formation of the swellable material.

"Re-embedding" the expanded sample in a non-swellable material comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the enlarged sample, for example, is embedded in the non-swellable material. Embedding the expanded sample in a non-swellable material prevent conformational changes (e.g., shrinkage) during the following steps despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In certain embodiments, the sample of interest, or a labeled sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

After the sample has been anchored to the polymer, the sample may be subjected to a disruption of the endogenous biological molecules or the physical structure of the biological sample. The disruption of the endogenous physical structure of the sample or of the endogenous biomolecules of the sample generally refers to the mechanical, physical, chemical, biochemical or, enzymatic digestion, disruption or break up of the sample so that it will not resist expansion. In this way, the mechanical properties of the sample-swellable material complex are rendered more spatially uniform, allowing greater and more consistent isotropic expansion.

It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample.

The expandable cell or tissue sample can be expanded by contacting the sample-polymer complex with a solvent or liquid to cause the polymer to swell. By expanding, or swelling, the expandable sample it is generally meant that the sample is physically expanded, or enlarged, relative to the sample prior to be exposed to the method(s) described herein.

The swelling of the swellable material results in the sample itself expanding (e.g., becoming larger). This is because the swellable material is embedded throughout the sample, therefore, by binding, e.g., anchoring, biomolecules to the swellable material and swelling, or expanding, the swellable material, the biomolecules are thereby moved apart. In one embodiment, the swellable material expands (swells) isotropically. As the biomolecules are anchored to the polymer network isotropic expansion of the polymer network retains the spatial orientation of the biomolecules resulting in an expanded, or enlarged, sample.

The expanded sample can then be subjected to microscopic analysis. By "microscopic analysis" it is meant the analysis of a sample using any technique that provides for the visualization of aspects of a sample that cannot be seen with the unaided eye, i.e., that are not within the resolution range of the normal eye.

The expanded sample-polymer complex can be imaged on any optical microscope, allowing effective imaging of features below the classical diffraction limit. Since the resultant expanded sample can be transparent, custom microscopes capable of large volume, wide field of view, 3D scanning may also be used in conjunction with the expanded sample.

Because biomolecules of the sample are anchored to a polymer that physically supports the ultrastructure of the sample, cellular components (e.g., lipids) that normally provide structural support but that hinder visualization of subcellular proteins and molecules may be removed while preserving the 3-dimensional architecture of the cells and tissue. This removal renders the interior of sample substantially permeable to light and/or macromolecules, allowing the interior of the sample, e.g., cells and subcellular structures, to be microscopically visualized without time-consuming and disruptive sectioning.

Additionally, the sample can be iteratively stained, unstained, and re-stained with other reagents for comprehensive analysis.

By "aliphatic group" it is generally meant, but not limited to, a non-aromatic moiety that may be saturated (e.g., single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

By "alkane group" it is generally meant, but not limited to, saturated hydrocarbons with the general formula $C_nH_{2n+2}$. They may be unbranched (normal) or branched. As used herein, the alkane is intended to include $C_1$-$C_{50}$ straight chain (linear) saturated aliphatic hydrocarbon groups and $C_3$-$C_{50}$ branched saturated aliphatic hydrocarbon groups. In embodiments, the alkane is intended to include $C_{15}$-$C_{35}$ straight chain (linear) saturated aliphatic hydrocarbon groups and $C_{15}$-$C_{35}$ branched saturated aliphatic hydrocarbon groups. In embodiments, the alkane is intended to include $C_{15}$-$C_{35}$ straight chain (linear) saturated aliphatic hydrocarbon groups.

By "fatty acid group" it is generally meant, but not limited to, a straight chain of an even number of carbon atoms, with hydrogen atoms along the length of the chain and at one end of the chain and a carboxyl group (—COOH) at the other end. In embodiments, the fatty acid can either be saturated, unsaturated or partially unsaturated.

By "biomolecules" it is generally meant, but not limited to, proteins, lipids, steroids, nucleic acids, and sub-cellular structures within a tissue or cell.

By "macromolecules" is meant proteins, nucleic acids, or small molecules that target biomolecules within the sample. These macromolecules are used to detect biomolecules within the sample and/or anchor the biolmolecules to the swellable polymer. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

As an example, the sample may be contacted with one or more polypeptide macromolecules, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. Peptides that are specific for a target cellular biomolecule and that are conjugated to a fluorophore or other detection moiety may also be employed.

Another example of a class of agents that may be provided as macromolecules is nucleic acids. For example, a sample may be contacted with an antisense RNA that is complementary to and specifically hybridizes to a transcript of a gene of interest, e.g., to study gene expression in cells of the sample. As another example, a sample may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e., agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

In some embodiments, the sample is subjected to passivation. As used herein the term "passivation" refers to the process for rendering the sample less reactive with the components contained within the fixative such as by functionalizing the fixative with chemical reagents to neutralize charges within. For example, the carboxylic groups of acrylate, which may be used in the swellable gel, can inhibit downstream enzymatic reactions. Treating the swellable gel composed of acrylate with 1-Ethyl-3-(3-dimethylaminopropyl)carbodiimide (EDC) and N-Hydroxysuccinimide (NHS) allows primary amines to covalently bind the carboxylic groups to form charge neutral amides and passivate the swellable gel.

Clinical tissue samples are usually highly fixed, tightly attached on the superfrost glass slides, and embedded in the paraffin (or stained and mounted in a mounting medium) for long-term storage. Some clinical tissue samples are stained with dyes, such as hematoxylin and eosin (H&E), which are incompatible with fluorescence imaging. To apply the instant invention to clinical samples, de-paraffinization, antigen retrieval and aggressive protease digestion are integrated in a comprehensive workflow to handle various kinds of common clinical samples. De-paraffinization and antigen retrieval address the recovery of archived clinical samples, while aggressive protease digestion is critical for the success of sample expansion, as most of the human tissues contain abundant hard-to-digest structural proteins, such as collagen and fibronectin, which prevent homogeneous expansion of the sample.

This invention provides a comprehensive workflow to facilitate expansion of common types of clinical samples for super-resolution molecular imaging. The methods described herein will result in optimal outcomes, such as proper immunostaining, sufficient digestion of tissue, high quality of polymer synthesis, and maintenance of proteins of interest during expansion.

The invention also describes the reutilization of classic H&E stained slides for further biomolecular interrogation in nanoscale level. In general, H&E stained slides are not considered suitable for further downstream processing due to the difficulty in removing the stain and mounting medium. Thus, the invention describes a unique and cost-effective approach to overcome this barrier and enable the extraction of more information from the used H&E slides. In one embodiment, the method of expanding H&E stained slides for further utilization combines xylene-ethanol-water sequential washing, protein anchoring and in situ polymer synthesis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc.

A whole brain and/or spinal cord specimen or region thereof (e.g. cerebrum (i.e., cerebral cortex), cerebellum (i.e., cerebellar cortex), ventral region of the forebrain (e.g., striatum, caudate, putamen, globus pallidus, nucleus accumbens; septal nuclei, subthalamic nucleus); regions and nuclei of the thalamus and hypothalamus; regions and nuclei of the deep cerebellum (e.g., dentate nucleus, globose nucleus, emboliform nucleus, fastigial nucleus) and brainstem (e.g., substantia nigra, red nucleus, pons, olivary nuclei, cranial nerve nuclei); and regions of the spine (e.g., anterior horn, lateral horn, posterior horn)) may be prepared post-mortem by the subject methods and the connectivity of the neurons therein microscopically analyzed, e.g., obtained, stored, rendered, used, and actuated, e.g., to provide the full connectivity of a brain, e.g., a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

The subject methods may also be used to evaluate normal tissues, organs and cells, for example to evaluate the relationships between cells and tissues of a normal tissue sample, e.g., a tissue sample taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult sample.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared sample microscopically analyzed for one or more cellular or tissue parameters. Parameters are quantifiable components of cells or tissues, particularly components that can be accurately measured, desirably in a high throughput system.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

The present invention will be better understood in connection with the following Examples. However, it should be understood that these examples are for illustrative purposes only and are not meant to limit the scope of the invention. Various changes and modifications will be apparent to those skilled in the art and such changes and modifications including, without limitation, those relating to the formulations and/or methods of the invention may be made without departing from the spirit of the invention and the scope of the appended claims.

EXAMPLES

The preprocessing steps of the ExM protocol were modified to better preserve lipids, since most lipids are not fixed during conventional chemical fixation[16]. To achieve lipid retention, two practices were introduced during tissue preservation and preparation for ExM. First, paraformaldehyde was combined with a low percentage (0.1%; increasing this number to 0.2% lowered the expansion factor, indicating incomplete tissue homogenization) of glutaraldehyde during fixation, since the latter helps to stabilize lipids (likely via stabilizing surrounding proteins[16]). Second, the temperature during tissue processing was maintained at 4° C. (processing at room or higher temperatures decreased lipid signals), since lipid loss can be exacerbated by higher temperatures[17], but at low temperatures lipids are in a more ordered state and are less likely to diffuse out of the sample[18]. In more detail: brain tissue was preserved in 4% paraformaldehyde (PFA) with 0.1% glutaraldehyde in ice cold phosphate buffered solution (PBS), sectioned the brain and washed out excess aldehydes, then applied the membrane probe (still at 4° C.) at 100 μM final concentration. Incubation at higher than 100 μM probe concentrations yielded no change in the observed signal. AcX was then added at 4° C. to make the membrane probes hydrogel-anchorable and incubated the specimen with the ExM gel monomer solution at 4° C. Finally the samples were incubated at 37° C. to initiate free-radical polymerization based hydrogel formation (Table 1).

TABLE 1

Monomer solution aka StockX (9.4 ml, aliquoted to 10 tubes of 940 μl and stored at −20° C.):

| Reagent | Stock concentration* | Amount (ml) |
|---|---|---|
| Sodium Acrylate (Sigma, cat. no. 408220) | 38 | 2.25 |
| Acrylamide (Sigma, cat. no. A8887) | 50 | 0.5 |
| N,N'-Methylenebisacrylamide (Sigma, cat. no. M7279) | 2 | 0.75 |
| Sodium chloride (Thermo Fisher, cat. no. BP358-212) | 29.2 | 4 |
| PBS (Thermo Fisher, cat. no. 70011044) | 10x | 1 |
| Water (Thermo Fisher, cat. no. 10977015) |  | 0.9 |
| Total |  | 9.4 |

Polymerization solution (1 ml, prepared at 4° C., gelled at 37° C.):

| Reagent | Stock concentration* | Amount (μl) |
|---|---|---|
| Monomer Solution (see above) | 1x | 940 |
| 4-hydroxy-TEMPO (Sigma, cat. no. 176141) | 0.5 | 20 |
| TEMED (Sigma, cat. no. T7024) | 10 | 20 |
| APS (Thermo Fisher, cat. no. 17874) | 10 | 20 |
| Total |  | 1000 |

Digestion buffer* (100 ml, prepared and stored at RT, applied at 37° C.):

| Reagent | Stock concentration | Amount |
|---|---|---|
| Tris pH 8.0 (Thermo Fisher, cat. no. AM9856) | 1M | 5 ml |
| EDTA (Thermo Fisher, cat. no. 15575020) | 0.5M | 0.2 ml |
| Triton X-100 (Sigma, cat. no. X100) | 10% | 5 ml |
| NaCl (Sigma, cat. no. S5886) | >99% solid | 5.85 g |
| Water (Thermo Fisher, cat. no. 10977015) |  | 84 ml |
| Total |  | 100 ml |

Fixation Reversal buffer (10 ml, prepared at RT and used immediately):

| Reagent | Stock concentration* | Amount |
|---|---|---|
| PEG20000 (Sigma, cat. no. 95172-250G-F) | 5% | 1 ml |
| DTT (Thermo Fisher, cat. no. R0862) | >97% solid | 154.3 mg |

TABLE 1-continued

| | | |
|---|---|---|
| SDS (Thermo Fisher, cat. no. AM9820) | 20% | 2 ml |
| Tris pH 8 (Thermo Fisher, cat. no. AM9856) | 1M | 1 ml |
| Water (Thermo Fisher, cat. no. 10977015) | | 5.9 ml |
| Total | | 10 ml |

*All concentrations are in g/100 ml except PBS. All stock solutions are formulated in water (Thermo Fisher, cat. no. 10977015).
*All concentrations are in g/100 ml except Monomer Solution. All stock solutions are formulated in water (Thermo Fisher, cat. no. 10977015).
*To formulate the Digestion solution, dilute Proteinase-K (NEB, cat. no. P8107S) at 1:100 dilution in Digestion buffer. All stock solutions are formulated in water (Thermo Fisher, cat. no. 10977015).
*All stock solutions are formulated in water (Thermo Fisher, cat. no. 10977015).

Gelled samples were homogenized with a digestion buffer containing proteinase K, and post-labeled with fluorescent streptavidin (FIG. 1A, top row). Except for the pre-processing, the remainder of the steps—incubation, gelation, digestion, and expansion—are identical to earlier ExM protocols such as proExM, ensuring even and isotropic expansion.

Figure 4:
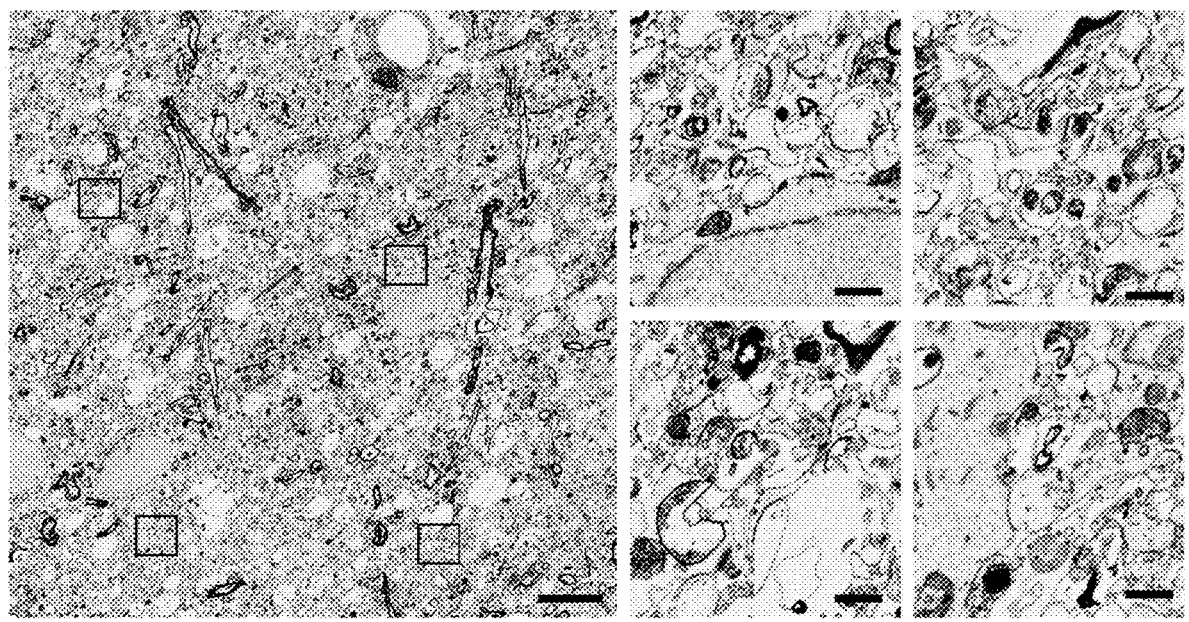
FIG. 4 Electron microscopy imaging of candidate membrane labels. 100 µM of farnesylated glycine pentalysine peptide was applied to 200 µm thick tissue slices from a mouse brain perfused with 4% PFA and 0.1% glutaraldehyde in 4° C., labelled with lipids for 2 days at 4° C. and labelled with 0.8 nm undecagold gold nanoparticles. In this case, and to achieve the smallest possible probe, we used the azide versions of the probe and conjugated it to dibenzocyclooctyne modified gold nanoparticles. The tissue was post-fixed in 2% glutaraldehyde, embedded in resin, counter-labeled with osmium tetraoxide and imaged. Osmium tetraoxide labeling appears as a grey outline of membranes whereas the lipid labels appear as darker black lines. The farnesylated version of the label only shows partial coverage. Scale bars: 10 µm for the low-resolution images, 1 µm for the high-resolution inserts.
Figure 5:
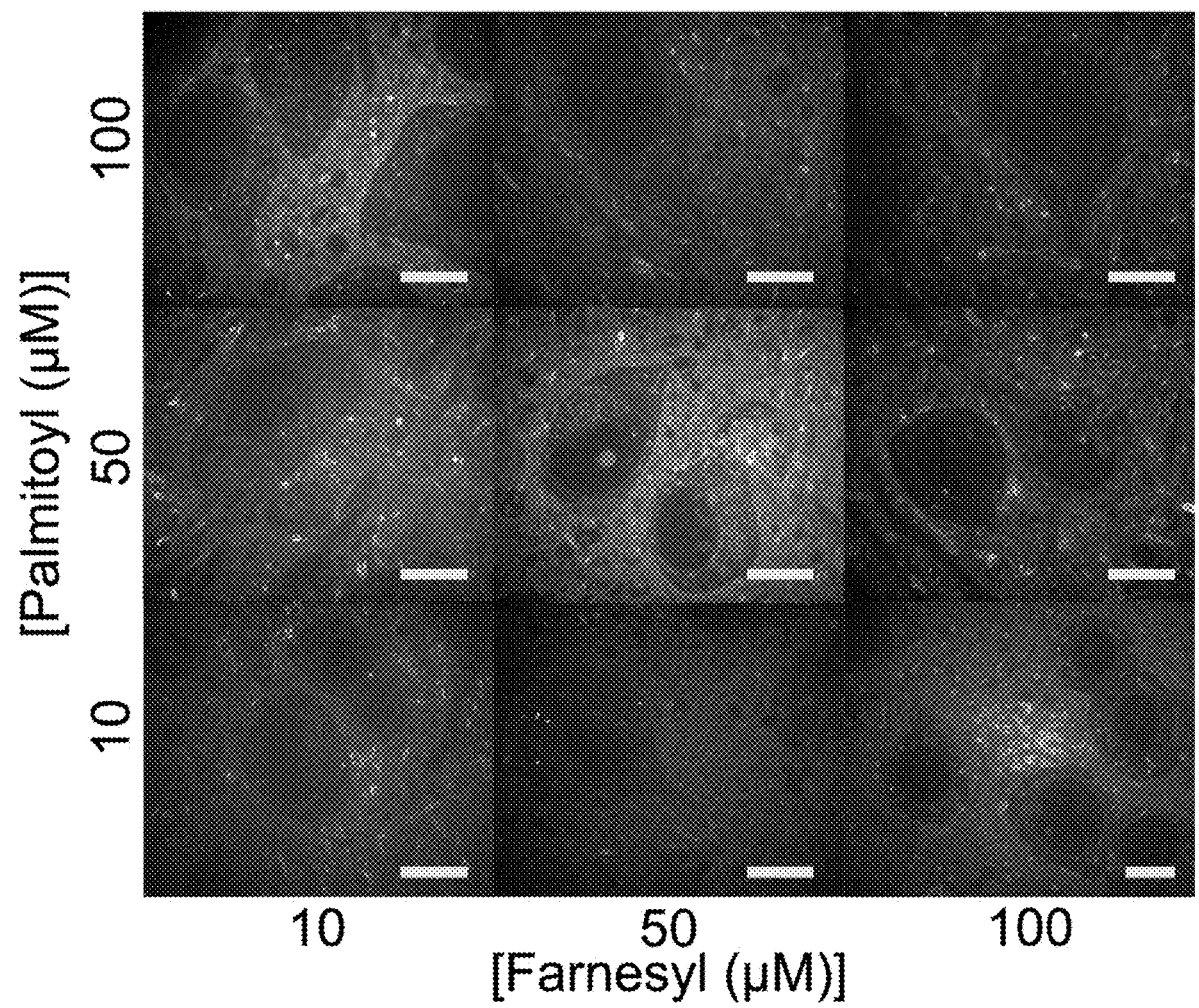
FIG. 5 Combinatorial screening of saturated (palmitoyl) and unsaturated (farnesyl) lipid peptides for membrane labeling. 100 µm thick brain tissue, fixed with 4% PFA and 0.1% glutaraldehyde, was incubated at varying concentrations of membrane label containing the two different lipid tails. The tissue was processed with AcX and a bis-acrylamide gel was formed. After tissue homogenization with proteinase K the membrane labels were stained with fluorescent streptavidin, expanded, and imaged. We examined whether combining saturated and unsaturated lipids at various concentrations would increase the membrane labeling yield, but did not observe a major difference. Especially at high concentrations, when combining the two probes, we observed an apparent weaker signal which may be due to either aggregation of the probes due to hydrophobicity or the formation of nanoparticles by them which hinders their diffusion. Scale bars represented in pre-expansion units: 10 µm.

Inspired by common lipid post-translational protein modifications, lipid tails that were both saturated and unsaturated were investigated—specifically palmitoyl[19] versus farnesyl[20] tails. To assess whether saturated vs. unsaturated lipid tails exhibited different performance, mouse brain tissue sections were incubated with 100 μM of palmitoylated vs. farnesylated forms of our lipid stain (with an azide replacing the biotin, for simplicity). The lipid stains were labeled with 0.8 nm gold nanoparticles modified with a dibenzocyclooctyne (DBCO) handle, and imaged the resulting specimens with an electron microscope. Membranes were counterstained with a "ground truth" electron microscopy label, osmium tetraoxide. These experiments showed that instant membrane labeling probe indeed labeled lipids (FIG. 1B), and also that the palmitoylated probe (FIG. 1B) achieved denser membrane labeling than the farnesylated one (FIG. 4). This pattern was borne out when the stains were compared using ExM (FIG. 5).

A palmitoyl and a farnesyl group were combined into a single backbone (on the N and C termini of the peptide, respectively), but observed limited tissue penetration, perhaps due to high hydrophobicity, as evidenced by probe accumulation on the surface of the tissue.

Figures 2A, 2B:
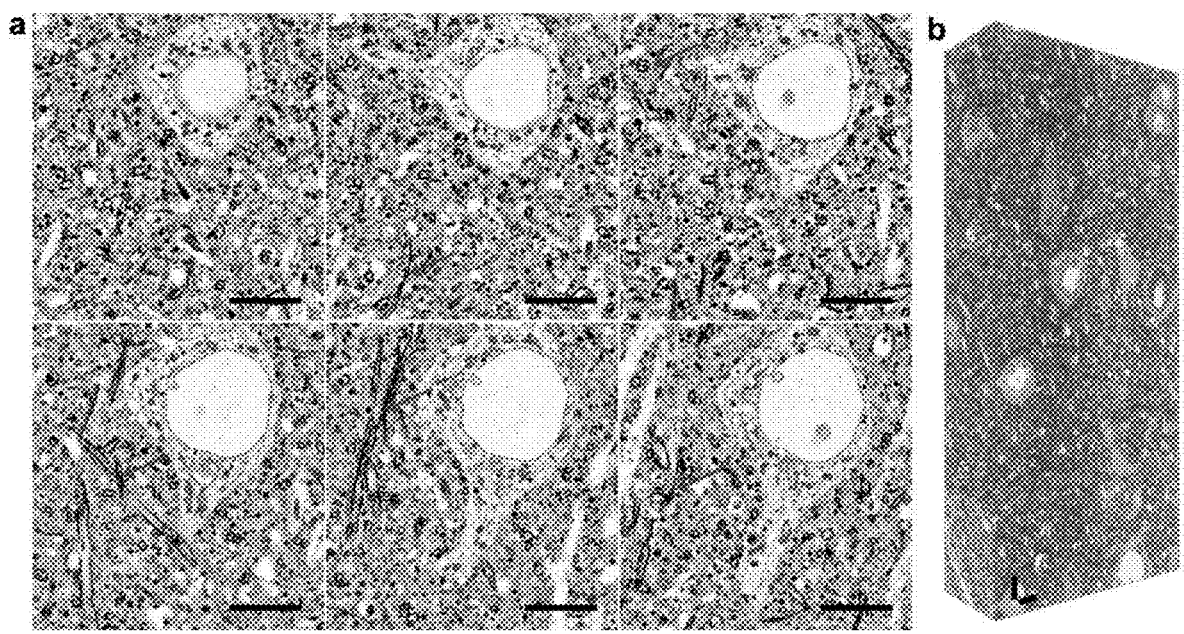
FIG. 2A and FIG. 2B. depict membrane expansion microscopy (mExM) of fixed brain tissue.
Figures 6A, 6B:
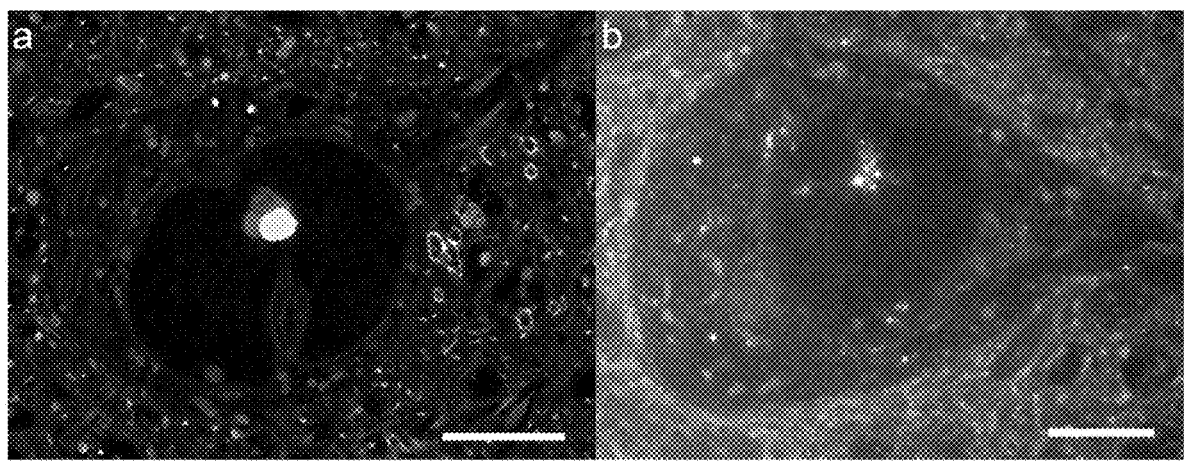
FIG. 6A and FIG. 6B. Effect of the glycine linker attached to the palmitoyl group on the efficacy of membrane labeling in fixed brain tissue. We tested two versions of the palmitoylated penta-lysine biotin membrane probe: a) one containing a glycine linker attached to the palmitoyl group enabling flexibility of the lipid relative to the peptide carrier and b) one that does not contain a glycine but in which the lipid is directly attached to the lysine backbone. In the case of the glycine linker, the level of detail we achieve in labeling membranes is superior to that achieved without the glycine linker. Scale bars represented in pre-expansion units: 5 µm.
Figure 7:
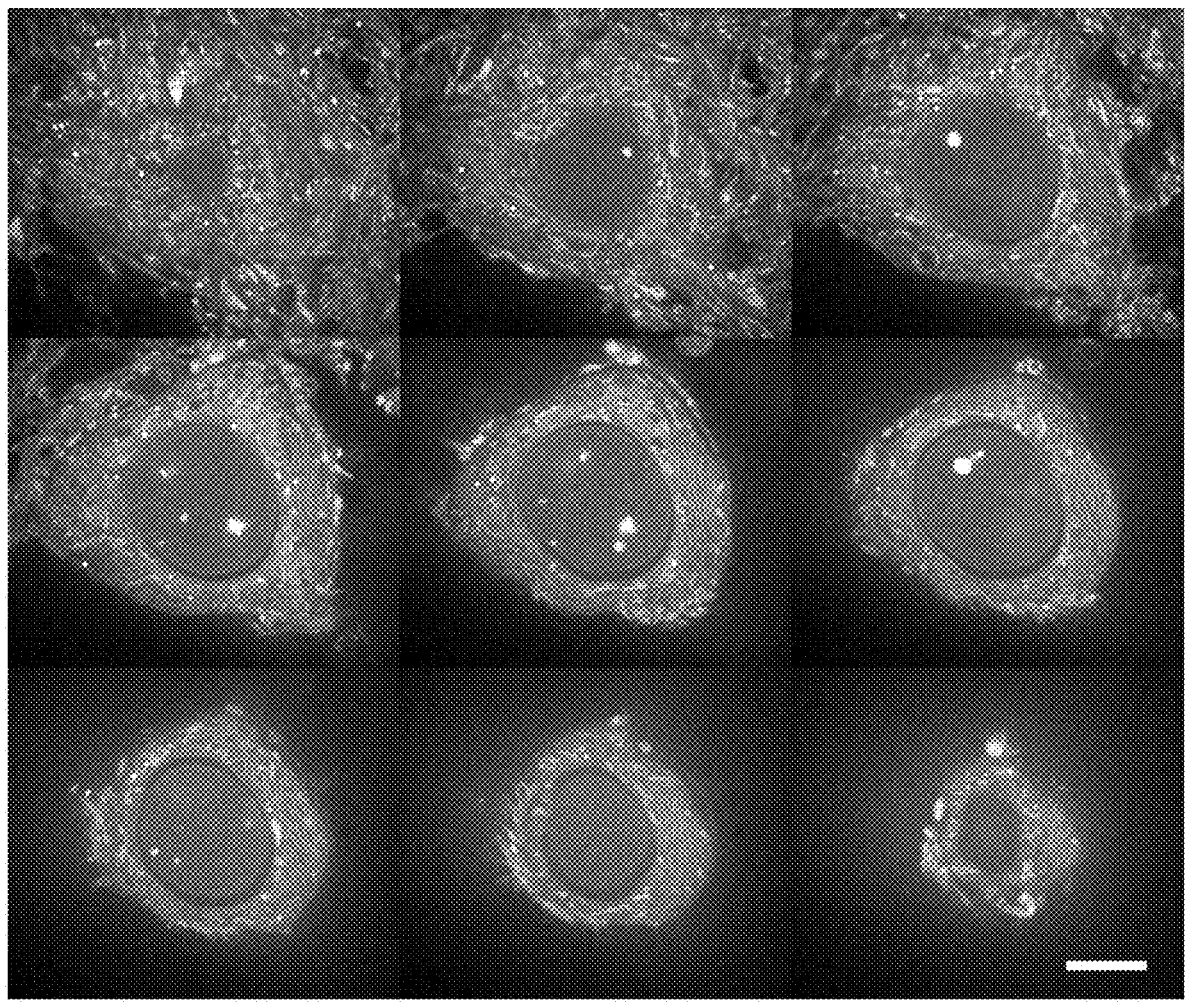
FIG. 7 Membrane labeling of a fixed HeLa cell cultured in vitro. HeLa cells were grown on coverslips and fixed with ice cold 4% PFA and 0.1% glutaraldehyde for a half hour in 4° C. The cells were washed overnight with PBS at 4° C. and 1 µM of pGk5b was applied in PBS at 4° C. for 6 hours. After applying AcX at 0.1 mg/ml in PBS for 8 hours at 4° C., a bis-acrylamide ExM gel was formed (as in the tissue processing form of mExM) and the samples were processed with proteinase K at 37° C. for 8 hours. The samples were labeled with streptavidin at 0.1 mg/ml concentration and then with fluorescent biotin at 0.2 mg/ml. After expansion in water the samples were imaged with a spinning disk confocal microscope. Nine different z-sections of a single stack captured 0.5 µm apart are displayed. We can achieve labeling of cellular organelles and membranes and image them with nanoscale resolution. Scale bar represented in pre-expansion units: 5 µm.

Versions of the probe with vs. without the glycine linker were assessed; omitting the glycine linker caused loss of detail (FIG. 6). The results of these chemical synthesis and screening steps was a glycine and penta-lysine D-peptidic backbone, with a palmitoyl lipid group on the amine-terminus and a biotin on the carboxy-terminus, with a molecular weight of 1216 Daltons, referred to herein as pGk5b (palmitoyl-G-kkkkk-biotin; [SEQ ID NO: 1]0 FIG. 1A, inset). The use of this lipid label, with lipid-preservation-optimized tissue fixation and processing as described in the previous paragraph, is referred to as membrane expansion microscopy (mExM).

mExM enabled dense labeling of membranous structures in the mouse brain that cannot be observed in unexpanded tissue (FIG. 1C). In addition to tissue specimens (FIG. 2), mExM can be used to label and expand membranes of fixed cells cultured in vitro (FIG. 7). Samples expand 4.5 times, as expected because the core (polymerization, digestion, and expansion) of the mExM process is identical to that of earlier ExM protocols such as proExM, which have been validated to expand isotropically (with few-percent error over length scales of tens to hundreds of microns) in many cell types and tissue types[3, 21, 22].

Immunohistochemistry-Compatible mExM

Figures 8A, 8B:
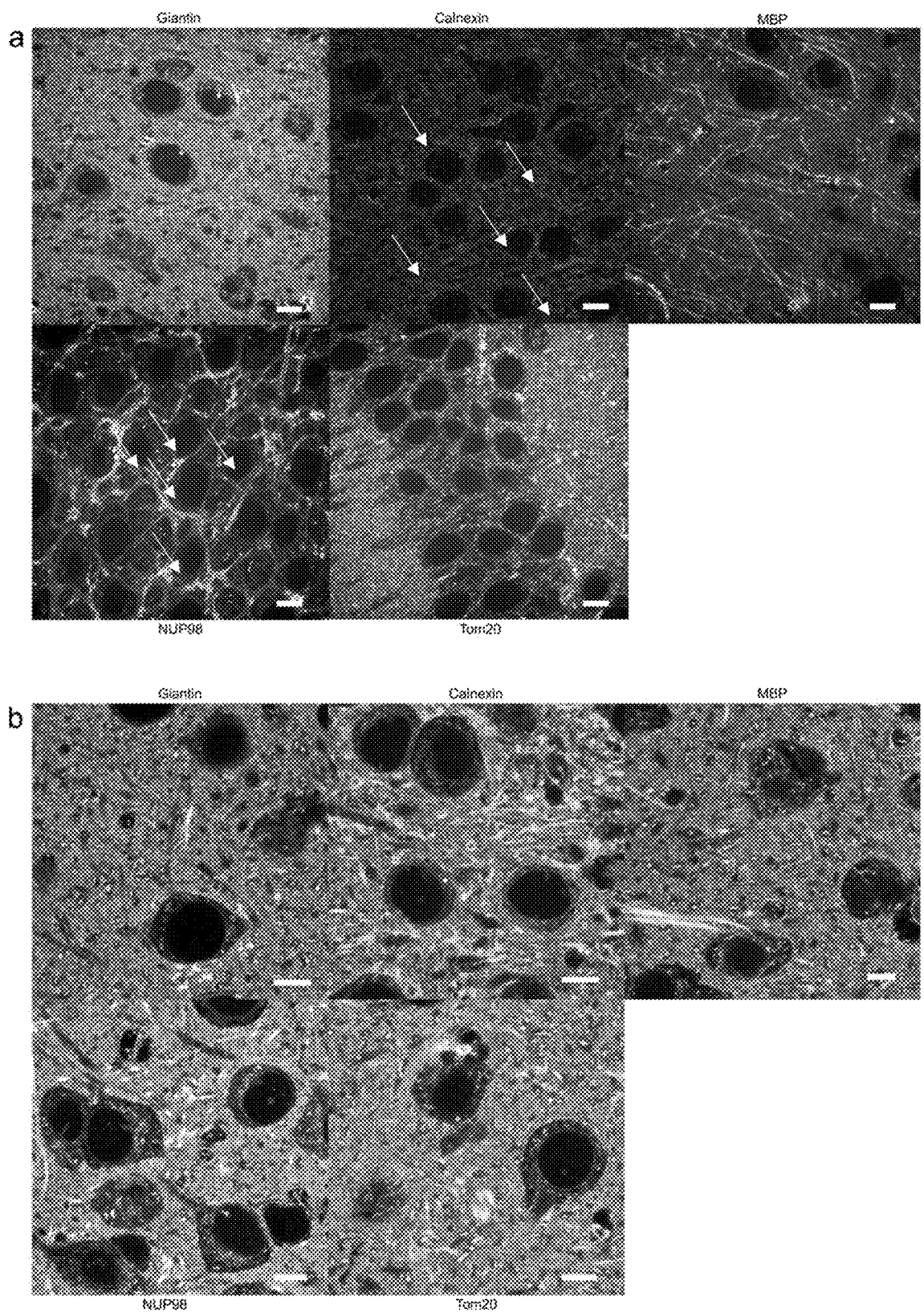
FIG. 8A and FIG. 8B Attempts to establish an antibody labeling procedure by synthesizing chemical meshes in an already-membrane labeled tissue. Considering that membrane and antibody labeling are not directly compatible, as during antibody labeling detergents dissolve lipid membranes, we tried to create a protocol for antibody labeling where after the membrane label application we create a chemical mesh holding those labels in place while performing common immunohistochemistry procedures. First (a) we applied the membrane labels to a 4% PFA and 0.1% glutaraldehyde fixed tissue and post-fixed with 0.1% PFA. After antibody labeling following established immunohistochemistry protocols including permabilization with detergents, we gelled the tissue, homogenized it with proteinase K and expanded. The lipids are color coded with black and white, and the antibody signal with red. We observed that not all of the antibodies labeled the epitopes correctly, for example calnexin labeling becomes non-specific (white arrows; the signal is non-specific) and NUP98 labeling is lost (white arrows; no signal on the nuclear membrane), and the tissue expanded only ~3-fold. Alternatively (b), after applying the membrane labels we created a non-expanding hydrogel, labeled with antibodies, created a second expanding hydrogel on top and after homogenization with proteinase K expanded the tissue. In that case we observed loss of labeling with antibodies and the tissue also expanded 3-fold. The loss of labeling may be due to the decrease of diffusivity of the antibodies imposed by the added non-expanding hydrogel. Scale bars represented in pre-expansion units: 10 μm.

Given the interactions between proteins and lipids, in support of the scaffolding of cellular signals and compartmentalization of signaling cascades, it would be desirable to jointly image lipids and proteins in the same specimen in an integrated protein and lipid ExM imaging protocol. Combining antibody staining and lipid labeling was not trivial: immunostaining protocols typically require permeabilization of samples with detergents, to enable penetration of antibodies throughout tissue[23], but detergents will also solubilize lipids and permeabilize membranes, preventing retention of the nanoscale spatial layout of the lipid membranes[24]. A variety of methods to resolve this issue were investigated. Using mild detergents (compared to those typical in immunofluorescence, e.g., Triton-X, NP-40, TWEEN) like saponin[25] resulted in antibody signals that looked punctate and dim, and compromise details of intracellular organelles. Therefore the lipid probes were immobilized before permeabilization and antibody labeling. Initially re-fixing the lipid probes by exposure to 0.1% PFA was attempted, but observed loss of epitope accessibility upon immunostaining, as well as low expansion factor (×2.8) (FIG. 8A). Alternatively, prior to forming the ExM gel, a cleavable but non-expanding hydrogel (containing only uncharged acrylamide, and crosslinked with the cleavable N,N'-diallyl-tartardiamide) was formed, that could anchor the lipid labels in place prior to detergent exposure, antibody staining, gelation with an expanding gel, cleavage of the initial gel and finally expansion of the second gel. However, in this case, the lipid staining was preserved, but antibody labeling was dim—presumably due to diffusion limitations arising from the non-expanding gel (FIG. 8B).

To solve these problems, a post-expansion antibody labeling protocol was developed, in which the tissue lipids were first labeled with a membrane labeling probe (e.g., pGk5b), synthesized the ExM gel, used high temperature and detergent (rather than epitope-destroying proteinase K) to perform the mechanical homogenization process[23] which allows isotropic expansion[3], and then delivered antibody labels to the retained epitopes after expansion. After this homogenization process but before replacing the buffer with pure water, to achieve full 4.5× expansion, the sample expands ~2 times in the antibody labeling buffer; thus we denote this procedure as "post-expansion antibody labeling".

The sample is heated for half an hour at 100° C. and for 2 hours at 80° C., in a "fixation reversal" (FR) buffer[28] containing 0.5% PEG20000, 100 mM DTT, 4% SDS, in 100 mM Tris pH8 (Table 2).

TABLE 2

| Antigen | Species | Company | Catalog no | Boiling (0.5 h@100° C., 2 h@80° C.) | Autoclaving (1 h@121° C.) |
|---|---|---|---|---|---|
| Calnexin | Rabbit | Abcam | ab22595 | ✓ | ✓ |
| Tom20 | Rabbit | CST* | 42406S | ✓ | ✓ |
| Tom20 | Mouse | SCBT** | sc-17764 | ✓ | ✗ |
| NUP98 | Rabbit | CST | 2597S | ✓ | ✓ |

TABLE 2-continued

| Antigen | Species | Company | Catalog no | Boiling (0.5 h@100° C., 2 h@80° C.) | Autoclaving (1 h@121° C.) |
|---|---|---|---|---|---|
| MBP | Rabbit | CST | 78896S | ✓ | ✓ |
| MBP | Chicken | AVES | AB_2313550 | ✓ | ✓ |
| Giantin | Rabbit | Biolegend | 924302 | ✓ | ✗ |
| Calreticulin | Rabbit | CST | 12238S | ✓ | ✗ |

*Cell Signaling Technology
**Santa Cruz Biotechnology
✓: Working
✗: Not working

Figures 3A, 3B, 3C, 3D, 3E:
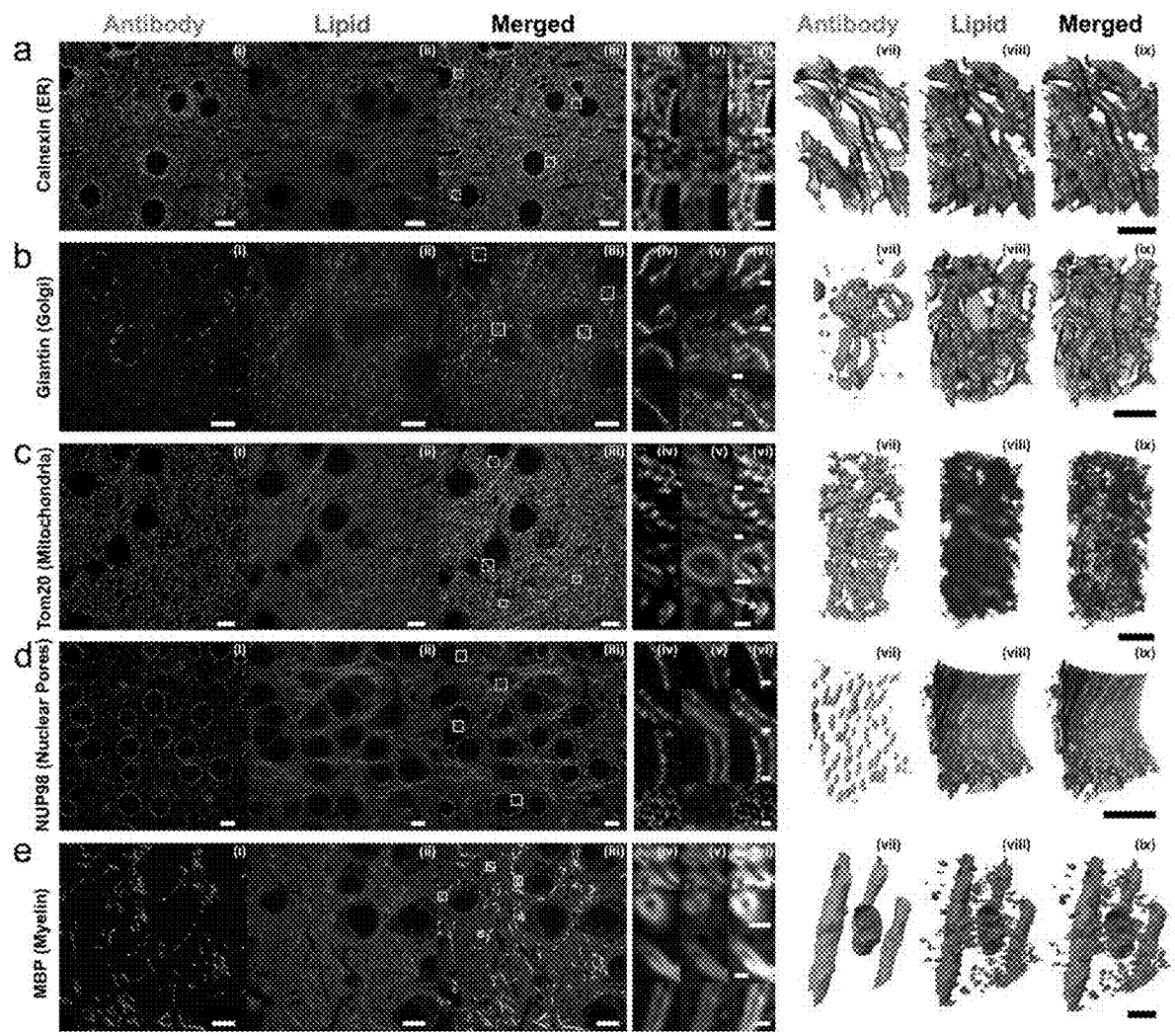
FIG. 3A through FIG. 3E. mExM enables simultaneous antibody and lipid co-visualization. After fixation and labeling with 100 µM pGk5b, mouse brain tissue is gelled and processed in the FR buffer (0.5% PEG20000, 100 mM DTT, 4% SDS, in 100 mM Tris pH8) by heating at 100° C. for 30 min, then 80° C. for 2 hr. After washing in PBS the gels are labeled with antibodies for (a) an endoplasmic reticulum surface protein (Calnexin), (b) a Golgi apparatus marker (Giantin), (c) a mitochondrial membrane protein (Tom20), (d) a nuclear pore complex component (NUP98), and (e) myelin (Myelin Basic Protein). (i-ii) Individual signals for antibodies (green) and membranes (magenta) and (iii) the overlay of (i) and (ii). (iv-vi) Details from the regions of (iii) indicated by squares. (iv) Antibody signal (green), (v) membrane signal (magenta) and (vi) the overlay of (iv) and (v). (vii-ix) Spatial visualization in 3D of lipid and antibody co-labeling with mExM. The membrane label is in magenta and antibodies in green. (a) Calnexin stains for rough endoplasmic reticulum and co-localizes with the membrane signal. Calnexin also co-localizes with the nuclear membrane signal (yellow arrows in vi). (b) Giantin is expressed on the surface of the Golgi apparatus and also co-localizes with membrane signals. (c) Mitochondrial staining is prevalent throughout the tissue and the Tom20 antibody signal overlaps with membrane labels. Tom20 appears to cluster at the mitochondrial membrane (arrow in vi). (d) Nuclear pore complexes span throughout the nuclear membrane. (e) Myelin basic protein co-localizes with the membrane signal and exhibits dense labeling, corresponding to the amount of lipid in highly myelinated regions of axons. Scale bars represented in pre-expansion units: (i-iii) 10 µm, (iv-vi) 1 µm. (vii-ix) Scale bars represented in pre-expansion units: 5 µm.
Figures 9A, 9B:
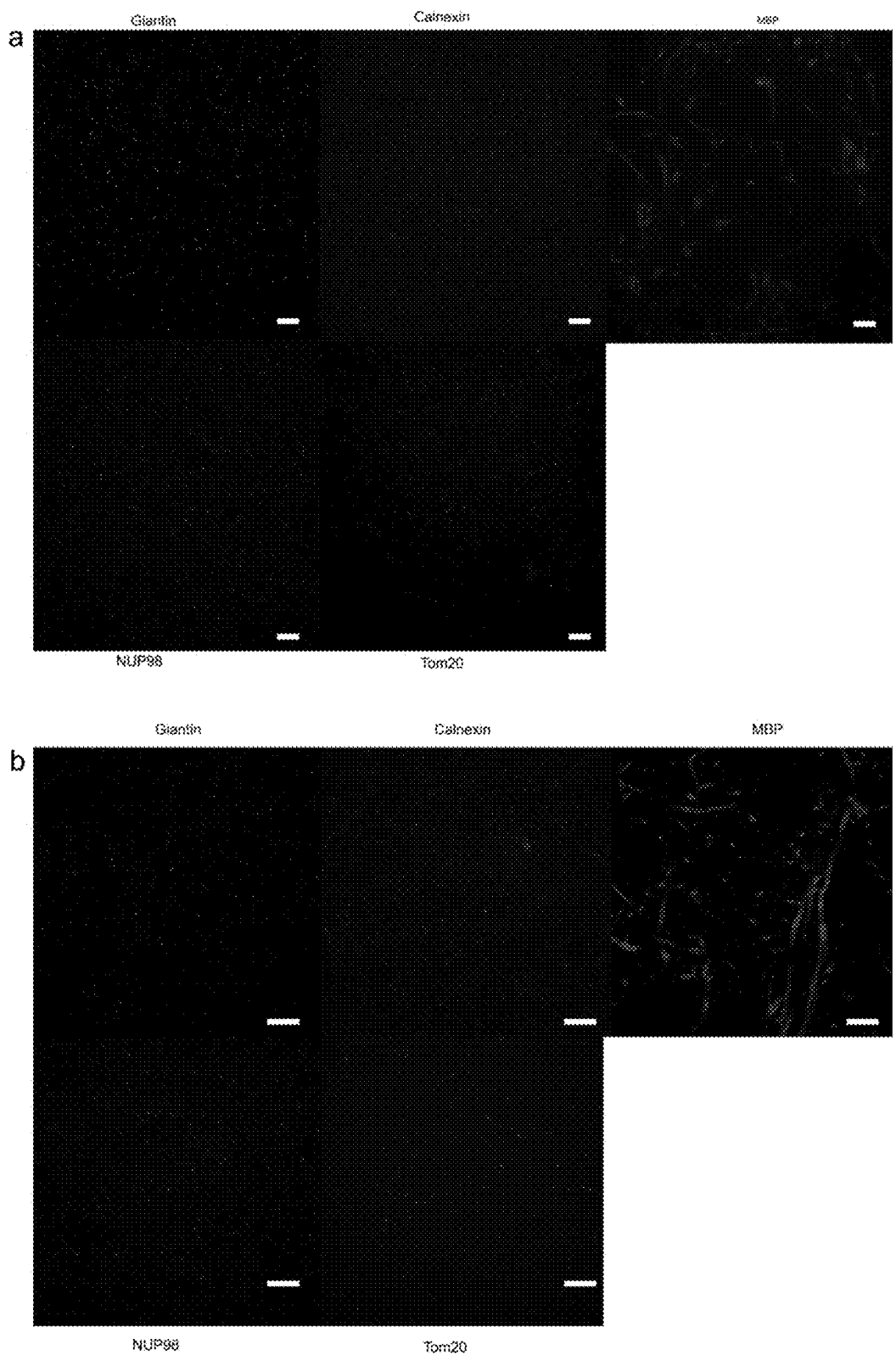
FIG. 9A and FIG. 9B Attempts to establish an antibody labeling procedure by processing the membrane labeled and gelled tissue with common antigen retrieval buffers. Fixed tissue was labeled for membranes with pGk5b and gelled. The gel-embedded tissue was thermally processed in a sodium citrate buffer (10 mM Sodium Citrate, 0.05% Tween 20, pH 6.0) (a) or tris buffer (10 mM Tris Base, 0.05% Tween 20, pH 10) (b), autoclaving at 121° C. for 1 hour. The gels were later labeled with antibodies and imaged. In both cases, we observed loss of antibody signal for most of the tested antibodies. Scale bars represented in pre-expansion units: 10 μm.

The FR buffer to work better than high-temperature treatment with alternative buffers (Citrate or Tris buffer for antigen retrieval) that caused loss of antibody staining (FIG. 9), or commercially available protein extraction buffers (i.e., RIPA buffer[29] and the Liquid Tissue MS Protein Prep Kit[30]) that did not support tissue expansion. Alternatively, the samples can be autoclaved at 121° C. for 1 hour in the FR buffer. In that case, and following the observations established for the post-expansion proExM method[3], some epitopes were not stained effectively by antibodies (Table 2), however, perhaps because of an interaction between the FR buffer and very high temperatures.

mExM was performed with antibody staining (FIG. 1A, bottom row), using antibodies against organelle-specific membrane-localized proteins—such as calnexin for the endoplasmic reticulum (ER, FIG. 3A), giantin for the Golgi apparatus (FIG. 3B), Tom20 for mitochondria (FIG. 3C), and NUP98 for the nuclear membrane (FIG. 3D). Myelin was also labeled using an antibody against myelin basic protein (FIG. 3E). In all cases, clear co-localization of the lipid signals from the membranes constituting the organelles was observed, with the antibody signals from the organelle membrane proteins.

The high resolution of mExM captured details of protein-lipid organization known to occur, but difficult or impossible to assess with conventional microscopy. For example, it is known that the endoplasmic reticulum contains components that come in close apposition with the nuclear membrane[31], which can be observed directly with ExM (FIG. 3A, right, yellow arrows). Specifically, Calnexin is a lectin protein expressed primarily on the surface of the rough ER[32], and a 3D representation of the iso-intensity profiles of Calnexin protein expression in the tissue reveals the cisternae of the ER and its co-localization with mExM-tagged ER lipids[33] (FIG. 3A(vii-ix)). Calnexin exhibits a peri-nuclear labeling pattern with co-localization with membrane labels—this represents a previously known sub-population of Calnexin proteins that are post-translationally modified with a palmitoyl group inside the ER and localize to contact sites of the ER with the nucleus[34]. Additionally, the Golgi apparatus, co-labeled with anti-giantin and our lipid stain, is visible primarily in neuronal somas, in accordance with previous studies[35] (FIG. 3B, right). In 3D, giantin labeling exhibits cisternal morphology that overlaps with pGK5b labeling (FIG. 3B(vii-ix)). Mitochondria are abundant throughout the tissue in somata, dendrites and axons. (FIG. 3C(vii-ix)). Tom20 expression on the surface of mitochondria reveals individual protein clusters, consistent with other super-resolution imaging methods (FIG. 3C, right, FIG. 3C(vi) yellow arrow). Nuclear pore complexes are resolved as individual pores on the nuclear membrane (FIG. 4, right), and can be seen to span the nuclear membrane when visualized in 3D (FIG. 3D(vii-ix)). Myelinated regions of neurons exhibit very strong membrane labeling (FIG. 3E, right), with excellent co-localization of the protein with the membrane label (FIG. 3E(vii-ix)).

In summary, a membrane intercalating probe is developed that enables the imaging of cellular membranes, in thick fixed tissue, in the context of a lipid-optimized form of expansion microscopy. Additionally, a post-expansion antibody labeling method was developed that allows for the joint imaging of proteins and membranes in ExM. This enables nanoscale observation of lipid membrane structures and their associated proteins at nanoscale resolution, even across large volumes, using ordinary microscopes. This will democratize and extend the study of membrane conformation and signaling in a wide range of biological systems in normal and disease states. Future directions may include the development of an iterative[2] form of mExM, in which a specimen is expanded twice (for a 4.5×4.5-20× physical magnification), which may enable resolutions of 10-20 nm, approaching that of electron microscopy, to be achieved.

Lipid Label Synthesis

The lipid labels were commercially synthesized (Anaspec). They were purified to >95% purity. They were aliquoted into 1 mg quantities in tubes, lyophilized to solid powder, and stored at −20° C. until stock solutions were prepared. For stock solutions, 1 mg of solid lipid label was dissolved in 50% DMSO and 50% ultrapure water to 10 mM and stored in −20° C.

Brain Tissue Preparation

Wild type (C57BL/6, Taconic) mice were first terminally anesthetized with isoflurane. Then, 1× phosphate buffered saline (PBS) was transcardially perfused until the blood cleared. For all mExM experiments, the mice were then transcardially perfused with the fixative 4% paraformaldehyde (PFA) and 0.1% glutaraldehyde, buffered in 1×PBS. The fixative was kept on ice during perfusion. After the perfusion step, brains were dissected out, stored in the fixative at 4° C. overnight for further fixation, and sliced on a vibratome (Leica VT1000S) at 100 μm or 200 μm thickness. The slices were then kept in 1×PBS at 4° C. overnight for washing and storing. All procedures involving animals were in accordance with the US National Institutes of Health Guide for the Care and Use of Laboratory Animals and approved by the Massachusetts Institute of Technology Committee on Animal Care.

mExM

Figure 10:
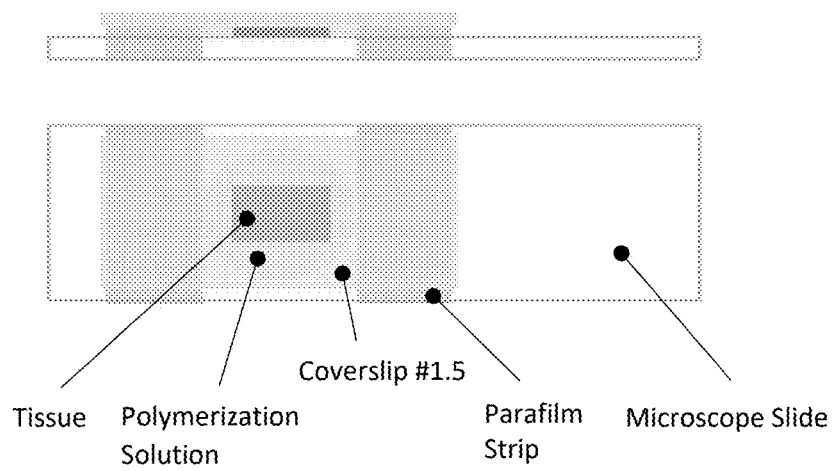
FIG. 10 The tissue polymerization chamber. To achieve polymerization, the tissue is set submerged in polymerization solution in between two pieces of glass: a microscope slide that serves as the base of the polymerization chamber, and a coverslip (thickness #1.5). To prevent compression of the tissue, the coverslip is set onto two strips of parafilm, which also prevent movement of the coverslip or leaking of the polymerization solution.

Tissue slices (100 μm for light microscopy and 200 μm for electron microscopy) were first incubated in the lipid labels (e.g., pGk5b) at 4° C. overnight to let the labels diffuse and intercalate thoroughly throughout the tissue slices. The lipid label 10 mM stock solution was diluted in 1×PBS that was kept at 4° C., at 1:100 dilution, for incubating the tissue slices. For a single piece of tissue 1 ml of solution was prepared. Subsequently, 6-((acryloyl)amino)hexanoic Acid, Succinimidyl Ester (AcX) stock solution (10 mg/mL in dimethylsulfoxide (DMSO)) was diluted in 1×PBS at 1:100 dilution, and tissue slices were incubated overnight at 4° C. The AcX stock solution was prepared by dissolving 5 mg AcX (ThermoFisher, catalog no. A20770) in 500 µl anhydrous DMSO (ThermoFisher, catalog no. D12345). It is essential that both these steps are carried out at 4° C. to keep the lipids in the tissue membranes thermodynamically stable. Then, the standard expansion microscopy steps were carried out. For formulations check Table 1. Briefly, for monomer solution we prepared Stock X and later added the polymerization initiator, accelerator and inhibitor. Recipe for Stock X: 8.6% (w/v) sodium acrylate (Sigma Aldrich, catalog no. 408220), 2.5% (w/v) acrylamide (Sigma Aldrich, catalog no. A8887-500G), 0.15% (w/v) N,N'-methylenebisacrylamide (Sigma Aldrich, catalog no. M7279-25G), 11.7% (w/v) sodium chloride (Thermo Fisher, catalog no. BP358-212), PBS). Recipes for the initiator, accelerator and inhibitor: 4-Hydroxy-TEMPO stock solution (4HT; Sigma Aldrich, catalog no. 176141), 0.5% (w/v) in water, N,N,N',N'-Tetramethylethylenediamine stock solution (TEMED; Sigma Aldrich, catalog no. T7024-50 ml), 10% (w/v) in water, and ammonium persulfate stock solution (APS; Thermo Fisher, catalog no. 17874), 10% (w/v) in water were prepared in advance and stored at −20 C. The gelation solution was prepared by mixing Stock X, 4HT, TEMED, and APS stock solutions in a 47:1:1:1 ratio on a 4° C. cold block, and the tissue slices that were incubated in the lipid labels and AcX were incubated in the gelation solution for 30 minutes at 4° C. During this step, the gelation chamber was constructed (FIG. 10). The chamber containing the tissue was then transferred over to an incubator kept at 37° C. to initiate free-radical polymerization. After 2 hours, the gelation chamber containing the tissue was taken out, and the gelled tissue was cut out from the chamber to be immersed in proteinase K digestion buffer. Proteinase K (ProK; NEB, catalog no. P8107S) was stored at −20° C. at 800 U/ml concentration, which was then diluted in the digestion buffer at 1:100 concentration prior to use. The digestion buffer was prepared by mixing: Triton X-100 (Sigma Aldrich, catalog no. 93426) to a final concentration of 0.5% (w/v) in water, EDTA disodium (0.5 M, pH 8, Thermo Fisher, catalog no. 15575020) to final 1 mM in water, Tris-HCl ((1 M) aqueous solution, pH 8, Life Technologies, catalog no. AM9855) to final 50 mM in water, and Sodium Chloride (Thermo Fisher, catalog no. BP358-212) to final 1M in water. The gelled tissue was then digested at 37 C on a shaker overnight. After digestion, the gelled sample was washed 4 times in 1×PBS at room temperature (RT), 30 minutes each. For imaging, the digested tissue was labelled with 0.3 mg/ml of streptavidin labelled with Atto 565 (Atto 565-Streptavidin; Sigma Aldrich, catalog no. 56304-1MG-F) buffered in 1×PBS overnight at RT, and then washed 4 times 30 minutes each in 1×PBS at RT before it was placed in excess water for expansion. The fluorescence of lipid labels were further amplified by labelling the gel once more with biotin labelled with Atto 565 (Atto 565-Biotin; Sigma Aldrich, catalog no. 92637-1MG-F) at 0.01 mg/ml concentration after the gel was incubated in Atto 565-Streptavidin and before it was immersed in excess water for expansion. Alternatively, instead of using Atto 565-Streptavidin, wild type streptavidin (Thermo Fisher, catalog no. S888) was used at 0.3 mg/ml with the same labelling conditions, and Atto 565 biotin was added at 0.01 mg/ml. The fluorescent labels attached to the biotin alone are sufficiently bright for imaging the sample with high signal-to-noise profiles.

Immunohistochemistry-Compatible mExM

The aforementioned mExM steps were carried out the same, except for the digestion step. Instead of using the proteinase K digestion buffer, tissue was boiled in the Fixation Reversal (FR) buffer for 30 minutes at 100° C. and then held for 2 hours at 80° C., or autoclaved for 1 hour at 121° C. The FR buffer consists of 0.5% PEG20000, 100 mM DTT, 4% SDS, in 100 mM Tris pH8. After this, the FR-digested sample was washed in 1×PBS 4 times at RT for 1 hour before proceeding to the standard immunohistochemistry steps. The sample was first blocked with MAXblock Blocking Medium (Active Motif, catalog no. 15252) for 4-6 hours at room temperature and incubated in MAXbind Staining Medium (Active Motif, catalog no. 15251) containing primary antibodies at a concentration of 10 µg/mL overnight at 4° C. Then, the sample was washed with MAXwash Washing Medium (Active Motif, catalog no. 15254) at RT 4 times, 30 minutes each and subsequently incubated in secondary antibodies buffered in MAXbind Staining Medium at a concentration of 10 µg/mL for 10-12 hours at 4° C. Finally, the secondary antibodies were washed, again, with MAXwash Washing Medium at RT 4 times, 30 minutes each time. For primary antibodies, anti-Calnexin (Abcam, catalog no. ab22595, Rabbit), anti-Tom20 (Cell Signaling Technology, catalog no. 42406S, Rabbit), anti-NUP98 (Cell Signaling Technology, catalog no. 2597S, Rabbit), anti-Giantin (Biolegend, catalog no. 924302, Rabbit), anti-Myelin Basic Protein (MBP; Cell Signaling Technology, catalog no. 78896S, Rabbit), were used. For secondary antibodies, anti-Chicken Alexa Fluor Plus 488 (Thermo Fisher, catalog no. A32931), anti-Rabbit Alexa Fluor Plus 488 (Thermo Fisher, catalog no. A32731), and anti-Mouse Alexa Fluor Plus 647 (Thermo Fisher, A32728) were used. After antibody staining, the lipid labels that were conjugated to the gel were then labelled with streptavidin and biotin containing Atto 565 fluorophores, as described in the mExM protocol mentioned above.

Confocal and Light-Sheet Imaging

All mExM images (FIGS. 2A, 3, 5, 6, 7, and 8) were taken with an Andor spinning disk (CSU-W1 Tokogawa) confocal system on a Nikon Eclipse Ti-E inverted microscope body with a 40× 1.15 NA water-immersion objective. Light-sheet imaging (FIG. 2B) was performed with a Zeiss Z.1 Light-Sheet microscope, utilizing a 20× 1.0 NA water immersion lens.

Expansion Factor Measurement

To determine the expansion factor for all mExM experiments, two procedures were followed. First, the distance between two landmarks in the whole tissue specimen was measured and compared before and after the expansion. Second, the tissue thickness, as measured by imaging the fluorescent labels across the vertical section of the specimen on a microscope, was determined and compared before and after expansion. The expansion factors that were obtained following these two ways were then averaged to be able to determine the expansion factor of an mExM experiment.

Image Processing

Images shown in FIGS. 2 and 3 were first filtered by a Gaussian filter, and then processed by the CLAHE algorithm[37] to remove possible noise. Image processing was performed with a 64 GB RAM, 8 core CPU desktop.

Electron Microscopy of Lipid Labeled Tissue

A terminally isoflurane anesthetized mouse was transcardially perfused with 1× phosphate buffered saline (PBS) at 4° C. until the blood cleared, followed by 4% PFA and 0.1% glutaraldehyde at 4° C. The tissue was post-fixed in the same solution (4% PFA and 0.1% glutaraldehyde in 4° C.) overnight. The tissue was sectioned into 200 µm thick slices using a vibratome (Leica VT1000 S) and washed in PBS, in 4° C. for a week. For each tissue section, 100 µM of palmitoylated glycine pentalysine peptide or 100 µM of farnesylated glycine pentalysine peptide was applied for 2 days at 4° C. and washed overnight in PBS at 4° C. In this case, and to achieve the smallest possible probe, we used the azide versions of the probes (i.e., the C-terminus of the peptide was modified with an azide). The membrane probes were post-labelled with 0.8 nm undecagold gold nanoparticles modified with a dibenzocyclooctyne. Briefly 50 nmole of amine modified 0.8 nm undecagold gold nanoparticles (Nanoprobes) diluted in PBS were incubated with 500 nmole of DBCO-NHS ester (Click Chemistry Tools) dissolved in DMSO overnight at room temperature. After the conjugation reaction the solution was further diluted to achieve <0.1% DMSO v/v in PBS and the reaction product was purified with dialysis in a membrane with 500 Da MWCO (SpectraPor/Spectrum).

The final product solution was concentrated in the dialysis membrane after submerging the membrane in a hygroscopic solution of 40% (w/v) PEG20,000 (Sigma Aldrich) in water to final volume 1 ml. The DBCO modified gold nanoparticles in PBS solution were applied to the membrane labeled tissue for 2 days at 4° C. The tissue was post-fixed in 2% glutaraldehyde, embedded in resin, counter-labeled with osmium tetraoxide and imaged. The tissue processing and imaging, post-membrane labeling, was performed at the electron microscopy facility at the Center of Brain Science at Harvard. Briefly, the tissue was counter-stained with reduced osmium tetroxide-thiocarbohydrazide-osmium and infiltrated with Epon resin. After curing, the tissue was sectioned to 30 nm thick slices using a commercial ultramicrotome (ATUM) and imaged with a Sigma scanning electron microscope (Carl Zeiss), equipped with the ATLAS software (Fibics).

Antibody Labeling in a "Non-Expanding" Gel

A terminally isoflurane anesthetized mouse was transcardially perfused with 1× phosphate buffered saline (PBS) at 4° C. until the blood cleared, followed by 4% PFA and 0.1% glutaraldehyde at 4° C. The tissue was post-fixed in the same solution (4% PFA and 0.1% glutaraldehyde in 4° C.) overnight. The tissue was sectioned into 100 µm thick slices in a vibratome (Leica VT1000 S) and washed in PBS, in 4° C. for a week. Tissue slices were incubated with the pGk5b lipid label at 4° C. overnight. Subsequently, 6-((acryloyl) amino)hexanoic Acid, Succinimidyl Ester (AcX) stock solution (10 mg/mL in dimethylsulfoxide (DMSO)) was diluted in 1×PBS that was kept at 4° C. at a 1:100 dilution, and the tissue slices were incubated in the diluted AcX solution. A non-expanding cleavable hydrogel was cast in the tissue. To prepare 9.4 ml of this gel monomer solution, we combined 2 ml of 50% (w/v) acrylamide (Sigma Aldrich) in water, 1.5 ml of 5% (w/v) N,N'-diallyl-tartardiamide (Bio-Rad) in water, 1 ml of 10×PBS and 4.9 ml of water. To initiate the polymerization reaction, to the 9.4 ml of monomer solution we added 200 µl of 0.5% (w/v) 4-hydroxy-TEMPO in water, 200 µl of 10% (w/v) TEMED in water and 200 µl of 10% (w/v) APS also in water. The monomer solution was kept on ice and incubation of the tissue slices in the monomer solution was performed at 4° C. for 30 min. Following the established ExM protocol the gel was formed in situ at 37° C. The sample was permeabilized in 1×PBS, 0.3% Triton-X buffer for 2 hours at room temperature and then blocked in blocking buffer (1×PBS, 5% Normal Donkey Serum, 0.3% Triton-X) for 4-6 hours also at room temperature. Antibodies were diluted according to the above Materials and Methods section in antibody dilution buffer (1×PBS, 1% Normal Donkey Serum, 0.3% Triton-X) and applied to the samples for 10-12 hours at room temperature. After washing for 4 hours in 1×PBS, 0.3% Triton-X and changing the washing buffer every 30 minutes, secondary antibodies were added in the same antibody dilution buffer for 10-12 hours at room temperature and at the same concentration as already stated in the Materials and Methods above. The membrane labels were counter-stained with fluorescent streptavidin similarly to the mExM protocol and washed for 2 hours at room temperature with PBS. Subsequently AcX (final concentration 0.1 mg/ml in PBS) was applied to the samples at 4° C. overnight. A new non-cleavable expanding gel was formulated on top of the cleavable non-expanding gel. For that, Stock X solution was formulated similarly to the Materials and Methods above and 4HT/TEMED/APS was added. The samples were incubated with that solution for 45 minutes at 4° C. and gelled according to the procedure mentioned in the Materials and Methods above. The double gelled samples were digested with proteinase K as above, overnight at 37° C. The first non-expanding gel was cleaved by incubating the samples in 20 mM sodium periodate (Sigma Aldrich, cat #71859), pH 5.5 in PBS, for 30 minutes at 37° C. The gel was subsequently washed in PBS, overnight at 4° C., and the signal from the membrane labels was amplified by labelling the gel once more with fluorescently labelled biotin as mentioned in the Materials and Methods above. After expanding the final gel in water, imaging was performed.

Antibody Labeling with Double Fixation

100 µm thick tissue slices were first incubated in the lipid labels (e.g., pGk5b) at 4° C. overnight to let the labels diffuse and intercalate thoroughly throughout the tissue slices. The lipid labels are stored at −20° C. in 10 mM stock concentration (in 50/50 water/DMSO mix), and they are diluted in 1×PBS that is kept at 4° C. at 1:100 dilution for incubating the 100 µm thick tissue slices. After brief washing in PBS for 2 hours at 4° C., the tissue was fixed again in 0.1% PFA solution in PBS at 4° C. for 4 hours and washed in PBS overnight at 4° C. The sample was permeabilized in 1×PBS, 0.3% Triton-X buffer for 2 hours at room temperature and then blocked in blocking buffer (1×PBS, 5% Normal Donkey Serum, 0.3% Triton-X) for 4-6 hours also at room temperature. Antibodies were diluted according the above Materials and Methods section in antibody dilution buffer (1×PBS, 1% Normal Donkey Serum, 0.3% Triton-X) and applied to the samples for 10-12 hours at room temperature. After washing for 4 hours in 1×PBS, 0.3% Triton-X and changing the washing buffer every 30 minutes, secondary antibodies were added in the same antibody dilution buffer for 10-12 hours at room temperature and at the same concentration as already stated in the Materials and Methods above. The membrane labels were counter-stained with fluorescent streptavidin similarly to the mExM protocol and washed for 2 hours at room temperature with PBS. The gelled samples were digested with proteinase K as above, overnight at 37° C. They were washed in PBS for 2 hours at room temperature. The signal from the membrane labels was amplified by labelling the gel once more with fluorescently labelled biotin as mentioned in the Materials and Methods above. After expanding the final gel in water, imaging was performed.

Antibody Labeling with Saponin

100 µm thick tissue slices were first incubated in the lipid labels (e.g., pGk5b) at 4° C. overnight to let the labels diffuse and intercalate thoroughly throughout the tissue slices. The lipid labels are stored at −20° C. in 10 mM concentration (in 50/50 water/DMSO mix), and they are diluted in 1×PBS that is kept at 4° C. at 1:100 dilution for incubating the 100 µm thick tissue slices. After brief washing in PBS for 2 hours at 4° C., the sample was first permeabilized in 1×PBS, 0.1% saponin for 2 hours at room temperature and then blocked in blocking buffer (1×PBS, 5% Normal Donkey Serum, 0.1% saponin) for 4-6 hours also at room temperature. Antibodies were diluted according the above Materials and Methods section in antibody dilution buffer (1×PBS, 1% Normal Donkey Serum, 0.1% saponin) and applied to the samples for 10-12 hours at room temperature. After washing for 4 hours in 1×PBS, 0.1% saponin and changing the washing buffer every 30 minutes, secondary antibodies were added in the same antibody dilution buffer for 10-12 hours at room temperature and at the same concentration as already stated in the Materials and Methods above. The membrane labels were counter-stained with fluorescent streptavidin similarly to the mExM protocol and washed for 2 hours at room temperature with PBS. The gelled samples were digested with proteinase K as above, overnight at 37° C. They were washed in PBS for 2 hours at room temperature. The signal from the membrane labels was amplified by labelling the gel once more with fluorescently labelled biotin as mentioned in the Materials and Methods above. After expanding the final gel in water, imaging was performed.

While this invention has been particularly shown and described with references to preferred embodiments thereof, it will be understood by those skilled in the art that various changes in form and details may be made therein without departing from the scope of the invention encompassed by the appended claims.

4. The membrane labeling probe of claim 3, wherein the hydrophobic group is palmitoyl.

5. The membrane labeling probe of claim 1, wherein the polymer anchorable group comprises about 2 to about 10 amino acids.

6. The membrane labeling probe of claim 1, wherein the polymer anchorable group comprises about 3 to about 6 amino acids.

7. The membrane labeling probe of claim 1, wherein the polymer anchorable group comprises about 5 amino acids.

8. The membrane labeling probe of claim 1, wherein the 2 or more amino acids are lysine.

9. The membrane labeling probe of claim 1, wherein the 2 or more amino acids are D-amino acids.

10. The membrane labeling probe of claim 1, wherein the label binder is biotin.

11. The membrane labeling probe of claim 1, wherein the membrane labeling probe comprises the formula palmitoyl-glycine-lysine-lysine-lysine-lysine-lysine-biotin (SEQ ID NO: 1).

12. A method for enlarging a sample of interest, the method comprising the steps of:
 contacting the sample with the membrane labeling probe according to claim 1;
 embedding the sample with the membrane labeling probe in a swellable material;
 subjecting the sample in the swellable material to a disruption of the endogenous physical structure of the sample; and
 swelling the swellable material to produce an enlarged sample.

What is claimed is:

1. A membrane labeling probe comprising the Formula A-B-C-D, wherein A is a hydrophobic group, B is a linker, C is a polymer anchorable group, and D is a label binder, wherein the linker is glycine, the polymer anchorable group comprises 2 or more amino acids, and the 2 or more amino acids are the same.

2. The membrane labeling probe of claim 1, wherein the hydrophobic group is a tween, an aliphatic group, an alkane group or a fatty acid group.

3. The membrane labeling probe of claim 2, wherein the hydrophobic group is a fatty acid group.

13. The method according to claim 12, wherein embedding the sample with the membrane labeling probe in the swellable material comprises:
 permeating the sample with the membrane labeling probe with a composition comprising one or more water soluble monomer precursors; and
 polymerizing the composition within the sample with the membrane labeling probe to form a sample-swellable material complex,
 wherein the polymerizing results in anchoring of the membrane labeling probe to the swellable material to form the sample-swellable material complex.

14. The method according to claim 13, wherein the composition comprises at least one polyelectrolyte monomer and a covalent crosslinker.

15. The method according to claim 12, wherein the swellable material is a hydrogel.

16. The method according to claim 15, wherein the hydrogel is a polyacrylate hydrogel.

17. The method according to claim 15, wherein the swellable material comprises acrylate, acrylamide, and a crosslinker selected from N,N-methylenebisacrylamide (BIS), N,N'-(1,2-Dihydroxythylene)bisacrylamide) (DHEBA); and N, N'-Bis(acryloyl) cystamine (BAC).

18. The method according to claim 12, wherein swelling the swellable material comprises adding an aqueous solvent or liquid to cause the swellable material to swell.

19. The method of claim 18, wherein the aqueous solvent or liquid is water.

20. The method of claim 12, wherein prior to embedding the sample with the membrane labeling probe in the swellable material, treating the sample with the membrane labeling probe with a detergent.

21. The method of claim 12, further comprising of producing a high-resolution image of the enlarged sample by viewing the enlarged sample under a microscope.

22. The method of claim 12, further comprising of optically imaging the enlarged sample by viewing the enlarged sample under a microscope.

* * * * *

UNITED STATES PATENT AND TRADEMARK OFFICE
CERTIFICATE OF CORRECTION

PATENT NO. : 12,265,004 B2
APPLICATION NO. : 17/089003
DATED : April 1, 2025
INVENTOR(S) : Edward Stuart Boyden et al.

Page 1 of 1

It is certified that error appears in the above-identified patent and that said Letters Patent is hereby corrected as shown below:

In the Claims

Column 25, Claim 1, Line 2, "Bis" should read "B is"

Column 25, Claim 1, Line 3, "Cis" should read "C is"

Column 26, Claim 11, Lines 3-4, delete "(SEQ ID NO: 1)"

Column 27, Claim 17, Line 5, "N, N'-Bis(acryloyl) cystamine" should read "N,N'-Bis(acryloyl)cystamine"

Signed and Sealed this
Twentieth Day of May, 2025

Coke Morgan Stewart
*Acting Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: palmitoyl attached to G
<220> FEATURE:
<221> NAME/KEY: MISC_FEATURE
<222> LOCATION: (6)..(6)
<223> OTHER INFORMATION: biotin attached at the C-terminal K

<400> SEQUENCE: 1

Gly Lys Lys Lys Lys Lys
1               5
```